US010890575B2

(12) United States Patent
Inaba et al.

(10) Patent No.: US 10,890,575 B2
(45) Date of Patent: Jan. 12, 2021

(54) LUBRICANT DETERIORATION DETECTION DEVICE AND LUBRICANT DETERIORATION STATE EVALUATION METHOD

(71) Applicant: NSK Ltd., Tokyo (JP)

(72) Inventors: Takenobu Inaba, Fujisawa (JP); Koichi Hachiya, Fujisawa (JP); Taisuke Maruyama, Fujisawa (JP)

(73) Assignee: NSK Ltd., Tokyo (JP)

( * ) Notice: Subject to any disclaimer, the term of this patent is extended or adjusted under 35 U.S.C. 154(b) by 80 days.

(21) Appl. No.: 16/089,742

(22) PCT Filed: Apr. 26, 2017

(86) PCT No.: PCT/JP2017/016541
§ 371 (c)(1),
(2) Date: Sep. 28, 2018

(87) PCT Pub. No.: WO2017/188314
PCT Pub. Date: Nov. 2, 2017

(65) Prior Publication Data
US 2019/0086382 A1    Mar. 21, 2019

(30) Foreign Application Priority Data

Apr. 28, 2016 (JP) ................................. 2016-091992
May 18, 2016 (JP) ................................. 2016-099725
(Continued)

(51) Int. Cl.
*G01N 33/28* (2006.01)
*F16N 29/00* (2006.01)
(Continued)

(52) U.S. Cl.
CPC ......... *G01N 33/2888* (2013.01); *F01M 11/10* (2013.01); *F16C 19/06* (2013.01);
(Continued)

(58) Field of Classification Search
CPC ........... G01N 33/2888; G01N 33/0047; G01N 33/0022; G01N 33/30; G01N 33/0004;
(Continued)

(56) References Cited

U.S. PATENT DOCUMENTS 6,324,899 B1    12/2001 Discenzo
8,916,728 B2 *  12/2014 Ruppin ................. C07C 213/00
                                                          560/265
(Continued)

FOREIGN PATENT DOCUMENTS

DE    10 2006 015 111 A1    10/2007
DE    10 2012 215 582 A1    3/2014
(Continued)

OTHER PUBLICATIONS

International Search Report (PCT/ISA/210) issued in PCT Application No. PCT/JP2017/016541 dated Jul. 25, 2017 with English translation (four (4) pages).
(Continued)

*Primary Examiner* — Harshad R Patel
*Assistant Examiner* — Nigel H Plumb
(74) *Attorney, Agent, or Firm* — Crowell & Moring LLP

(57) ABSTRACT

A lubricant deterioration detection device of the present invention includes a gas sensor that selectively detects a carbonyl compound. The gas sensor is configured to detect the carbonyl compound from at least one of formaldehyde, acetaldehyde, propanal, butanal, pentanal, n-hexanal, n-heptanal, formic acid, and acetic acid. The detection deteriora-
(Continued)

tion device further includes an oil removal portion that removes an oil mist generated from the lubricant.

7 Claims, 25 Drawing Sheets

(30) Foreign Application Priority Data

| | | |
|---|---|---|
| May 27, 2016 | (JP) | 2016-106694 |
| Feb. 15, 2017 | (JP) | 2017-026302 |
| Mar. 28, 2017 | (JP) | 2017-062682 |

(51) Int. Cl.

| | |
|---|---|
| *F16C 19/06* | (2006.01) |
| *G01N 33/00* | (2006.01) |
| *F16C 19/52* | (2006.01) |
| *G01N 33/30* | (2006.01) |
| *F16C 33/66* | (2006.01) |
| *F16N 29/04* | (2006.01) |
| *F01M 11/10* | (2006.01) |
| *F16C 41/00* | (2006.01) |
| *F16C 19/54* | (2006.01) |
| *H01L 35/32* | (2006.01) |

(52) U.S. Cl.
CPC .......... *F16C 19/52* (2013.01); *F16C 33/6625* (2013.01); *F16N 29/00* (2013.01); *F16N 29/04* (2013.01); *G01N 33/0009* (2013.01); *G01N 33/0022* (2013.01); *G01N 33/0047* (2013.01); *G01N 33/30* (2013.01); *F16C 19/54* (2013.01); *F16C 41/008* (2013.01); *F16C 2233/00* (2013.01); *F16N 2200/02* (2013.01); *F16N 2200/08* (2013.01); *F16N 2210/14* (2013.01); *F16N 2230/02* (2013.01); *F16N 2260/02* (2013.01); *F16N 2270/54* (2013.01); *H01L 35/32* (2013.01)

(58) Field of Classification Search
CPC ...... G01N 33/00; G01N 1/2273; G01N 19/02; G01N 29/02; F01M 11/10; F16C 19/06; F16C 33/66; F16N 29/00; F16N 29/54; F16N 29/52; B01D 37/00; B01D 35/005; B01D 35/26; B60R 17/00
See application file for complete search history.

(56) References Cited

U.S. PATENT DOCUMENTS

| | | | |
|---|---|---|---|
| 2002/0013635 A1 | 1/2002 | Gotou et al. | |
| 2003/0116509 A1* | 6/2003 | Manz | F16N 29/00 |
| | | | 210/745 |
| 2005/0072217 A1* | 4/2005 | Discenzo | G01N 11/00 |
| | | | 73/53.05 |
| 2012/0116126 A1 | 5/2012 | Ruppin et al. | |
| 2014/0165702 A1* | 6/2014 | Tanabe | G01N 29/022 |
| | | | 73/24.06 |
| 2016/0018381 A1* | 1/2016 | Potyrailo | G01N 27/026 |
| | | | 324/633 |

FOREIGN PATENT DOCUMENTS

| | | | |
|---|---|---|---|
| JP | 3-63238 | A | 3/1991 |
| JP | 2001-356808 | A | 12/2001 |
| JP | 2003-515707 | A | 5/2003 |
| JP | 2003-166696 | A | 6/2003 |
| JP | 2003166696 | * | 6/2003 |
| JP | 2007-292529 | A | 11/2007 |
| JP | 4029604 | B2 | 1/2008 |
| JP | 2009-92511 | A | 4/2009 |
| JP | 2009-155443 | A | 7/2009 |
| JP | 2012-136987 | A | 7/2012 |
| JP | 2012-163506 | A | 8/2012 |
| JP | 2012-530771 | A | 12/2012 |
| WO | WO 2011/069518 | A1 | 6/2011 |

OTHER PUBLICATIONS

Japanese-language Written Opinion (PCT/ISA/237) issued in PCT Application No. PCT/JP2017/016541 dated Jul. 25, 2017 (four (4) pages).
Japanese-language Office Action issued in counterpart Japanese Application No. 2017-544689 dated Jul. 3, 2018 with English translation (seven (7) pages).
International Preliminary Report on Patentability (PCT/IB/338 & PCT/IB/373) issued in PCT Application No. PCT/JP2017/016541 dated Nov. 8, 2018, including English translation of document C2 (Japanese-language Written Opinion (PCT/ISA/237) previously filed on Sep. 28, 2018) (seven (7) pages).
Extended European Search Report issued in counterpart European Application No. 17789596.8 dated Mar. 21, 2019 (four (4) pages).
Extended European Search Report issued in counterpart European Application No. 17789596.8 dated Apr. 16, 2019 (five (5) pages).
Chinese-language Office Action issued in counterpart Chinese Application No. 201780020847.8 dated Aug. 28, 2019 with English translation (15 pages).
Chinese-language Office Action issued in Chinese Application No. 201780020847.8 dated Feb. 21, 2020 with English translation (11 pages).

* cited by examiner 11 12 13 14

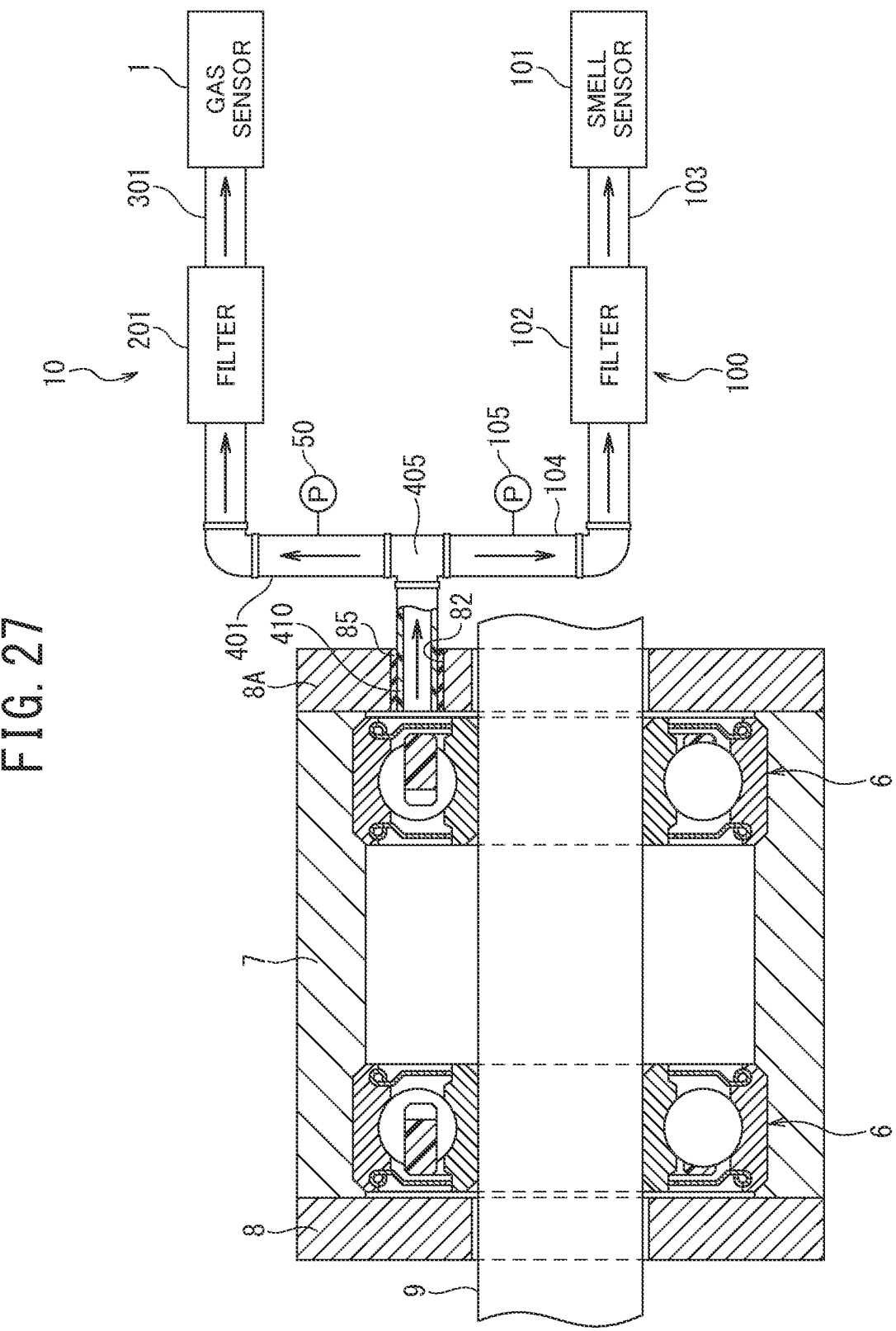

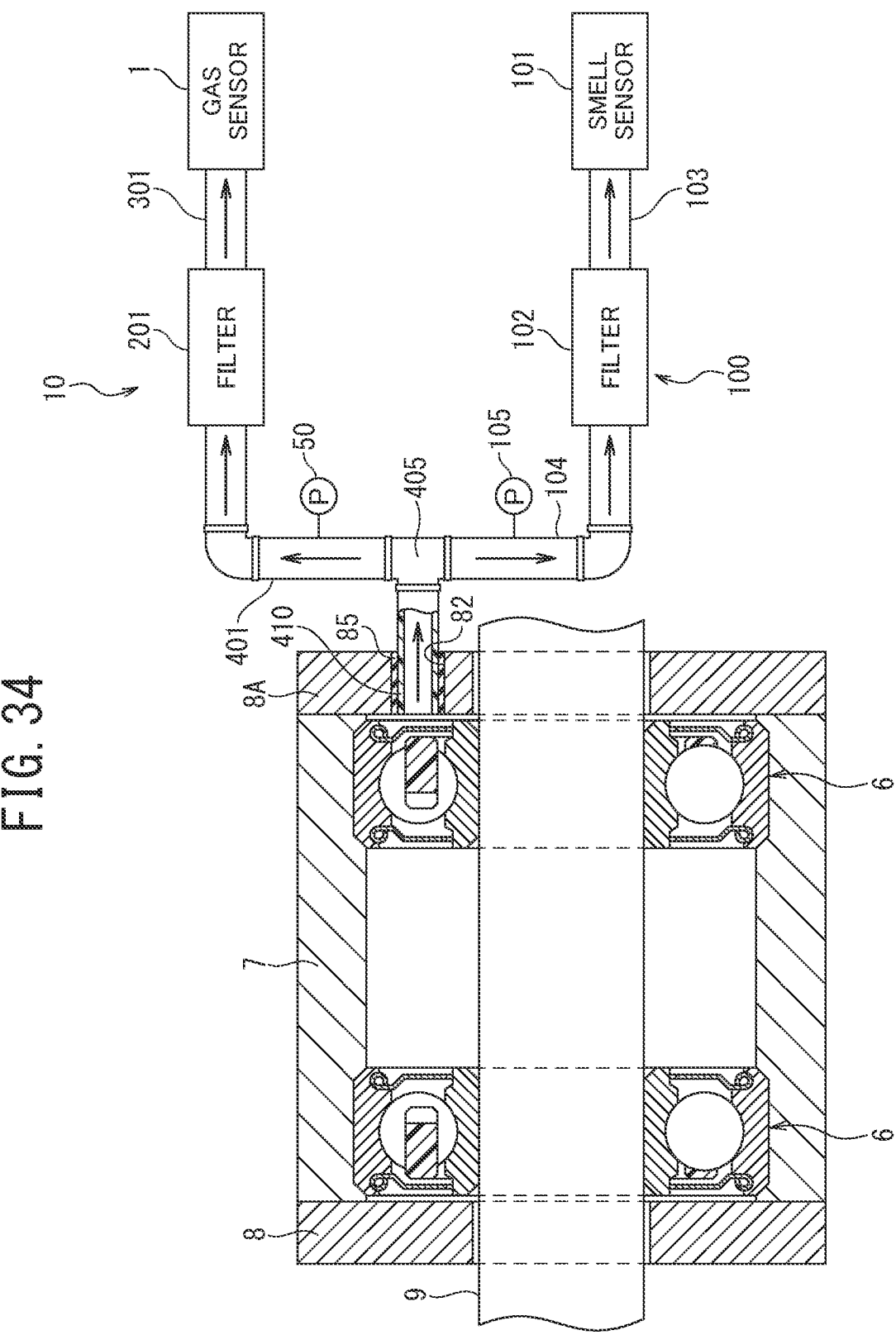

LUBRICANT DETERIORATION DETECTION DEVICE AND LUBRICANT DETERIORATION STATE EVALUATION METHOD

TECHNICAL FIELD

The present invention relates to a lubricant deterioration detection device and a lubricant deterioration state evaluation method.

BACKGROUND ART

In devices lubricated with a lubricant such as lubricating oil and grease, including rolling devices (for example, rolling bearings, ball screws, and linear guides), lubricant deterioration can increase the torque, the abrasion, the temperature, or the like of a device to cause abnormal events.

Deterioration of a lubricant is mainly caused by thermal decomposition and oxidation (oxidative deterioration), for example. Lubricant deterioration can lead to generation of acids, decomposition of lubricant components to generate volatile (low-molecular weight) hydrocarbons, generation of compounds having a carbonyl group (including a ketone group and an aldehyde group) or a similar group, and a reduction in thickness of a lubricating film to increase the abrasion amount of a lubrication-receiving member, for example.

Hence, measurement of the abrasion amount, the acid amount, the volatilization amount of hydrocarbons, and the amount of compounds having a carbonyl group or a similar group generated by deterioration enables determination of the deterioration state of a lubricant.

Conventionally, a lubricant is periodically sampled from a rolling device during operation, and the deterioration state of the lubricant is examined by the following method, for example. The method includes a method of measuring the abrasion amount by quantitative determination of a metal by atomic absorption analysis or the like, a method of measuring the acid amount by determination of the total acid value in accordance with "ASTM D3242", and a method of measuring the absorbance arising from a carbonyl group around 1,710 $cm^{-1}$ by infrared spectrophotometry.

Chemical deterioration of a lubricant proceeds from (1) peroxy radicals, (2) hydroperoxides, (3) carbonyl compounds, to (4) polymers (gum) and lower fatty acids, in this order. The method of measuring the acid amount is a method of detecting the deterioration in the step (4).

The method of periodically sampling a lubricant to examine the deterioration state, however, cannot prevent abnormal events when deterioration suddenly proceeds between examinations. Hence, there is a demand for enabling continuous monitoring of the deterioration degree of a lubricant in a rolling device.

PTL 1 discloses, as a device capable of continuous monitoring the deterioration state of a lubricant in a rolling bearing, a lubricant deterioration detection device including a gas sensor that detects at least any gas of hydrocarbons, hydrogen sulfide, and ammonia in a bearing. Specifically, a rolling bearing has a shield plate and is lubricated with a lubricant, a circular plate of the shield plate has an opening, and the gas sensor is attached to the opening through a ceramic filter.

PTL 1 also discloses a lubricant deterioration detection device in which an infrared generator and an infrared detector included in an infrared spectrometer are placed at opposite positions interposing a lubricant flowing pipe, and a sample cell through which infrared light passes is provided at a position of the pipe interposed between the infrared generator and the infrared detector. An example of the device is disclosed as a device that continuously monitors the deterioration state of a lubricating oil flowing in a pipe from a reservoir toward an oil supply opening for reuse of the lubricating oil discharged from a rolling bearing, by measuring the absorbance arising from a carbonyl group around 1,710 $cm^{-1}$.

CITATION LIST

Patent Literature

PTL 1: JP 4029604 B

SUMMARY OF INVENTION

Technical Problem

The lubricant deterioration detection device for a rolling bearing disclosed in PTL 1 includes a gas sensor that is directly attached to a shield plate and thus may malfunction by vibration or heat generated during operation of a bearing.

The lubricant deterioration detection device including an infrared spectrophotometer is difficult to accurately determine the absorbance of a carbonyl group generated by deterioration, directly from a lubricating oil in a pipe, and cannot be used when the lubricant is a grease.

In other words, the lubricant deterioration detection device disclosed in PTL 1 has room for improvement inaccurate determination of the lubricant deterioration.

The present invention is intended to enable determination of the deterioration state of a lubricant in a rolling bearing with high accuracy.

Solution to Problem

To solve the problems, a first aspect of the present invention provides a lubricant deterioration detection device including a gas sensor configured to detect a carbonyl compound.

A second aspect of the invention provides a lubricant deterioration detection device including a gas sensor configured to detect at least one of n-hexanal and n-heptanal.

A third aspect of the invention provides a lubricant deterioration state evaluation method including in situ determining an amount of a gaseous carbonyl compound generated from a lubricant in a rolling bearing lubricated with the lubricant to evaluate a deterioration state of the lubricant.

A fourth aspect of the invention provides a lubricant deterioration detection device that includes a housing rotatably storing a rolling bearing, a gas sensor located outside the housing, and a gas inlet pipe connecting a gas outlet port formed on the housing to a gas inlet port of the gas sensor and configured to introduce a gas in the housing into the gas sensor, and a deterioration state of a lubricant in the rolling bearing is detected by a detected value of the gas sensor.

Advantageous Effects of Invention

The lubricant deterioration detection device of the first aspect includes a gas sensor configured to detect a carbonyl compound that predicts deterioration of a lubricant, and thus more accurately determines lubricant deterioration than a device that determines lubricant deterioration by detection of hydrocarbons, which are generated even when a lubricant does not deteriorate yet.

The lubricant deterioration detection device of the second aspect includes a gas sensor configured to detect at least one of n-hexanal and n-heptanal that predicts deterioration of a lubricant, and thus more accurately determines lubricant deterioration than a device that determines lubricant deterioration by detection of hydrocarbons, which are generated even when a lubricant does not deteriorate yet.

According to the third aspect, a method capable of determining the deterioration state of a lubricant in a rolling bearing with high accuracy can be provided.

The lubricant deterioration detection device of the fourth aspect includes a gas sensor outside a housing that rotatably stores a rolling bearing, and thus the gas sensor is unlikely to be affected by vibration or heat generated during operation of the rolling bearing. Accordingly, the lubricant deterioration detection device can determine the deterioration state of a lubricant in a rolling bearing with higher accuracy than a lubricant deterioration detection device in which the housing of a gas sensor is directly attached to a rolling bearing.

BRIEF DESCRIPTION OF DRAWINGS

FIG. 27 is a view illustrative of a verification test method of lubricant deterioration detection performed in the third embodiment;

FIG. 34 is a view illustrative of a test method performed in the fourth embodiment;

DESCRIPTION OF EMBODIMENTS

First Aspect

[Discussion by Inventors]

The lubricant deterioration detection device disclosed in PTL 1 includes a gas sensor that detects at least any gas of hydrocarbons, hydrogen sulfide, and ammonia in a bearing.

However, the inventors of the present application have analyzed gases generated by thermal deterioration under long-term heating of a mineral oil, a poly-α-olefin oligomer oil, and a polyol ester oil used as a lubricant for bearings, with a gas chromatograph-mass spectrometer, revealing that the main component of smelling components is a carbonyl compound.

Figure 1:
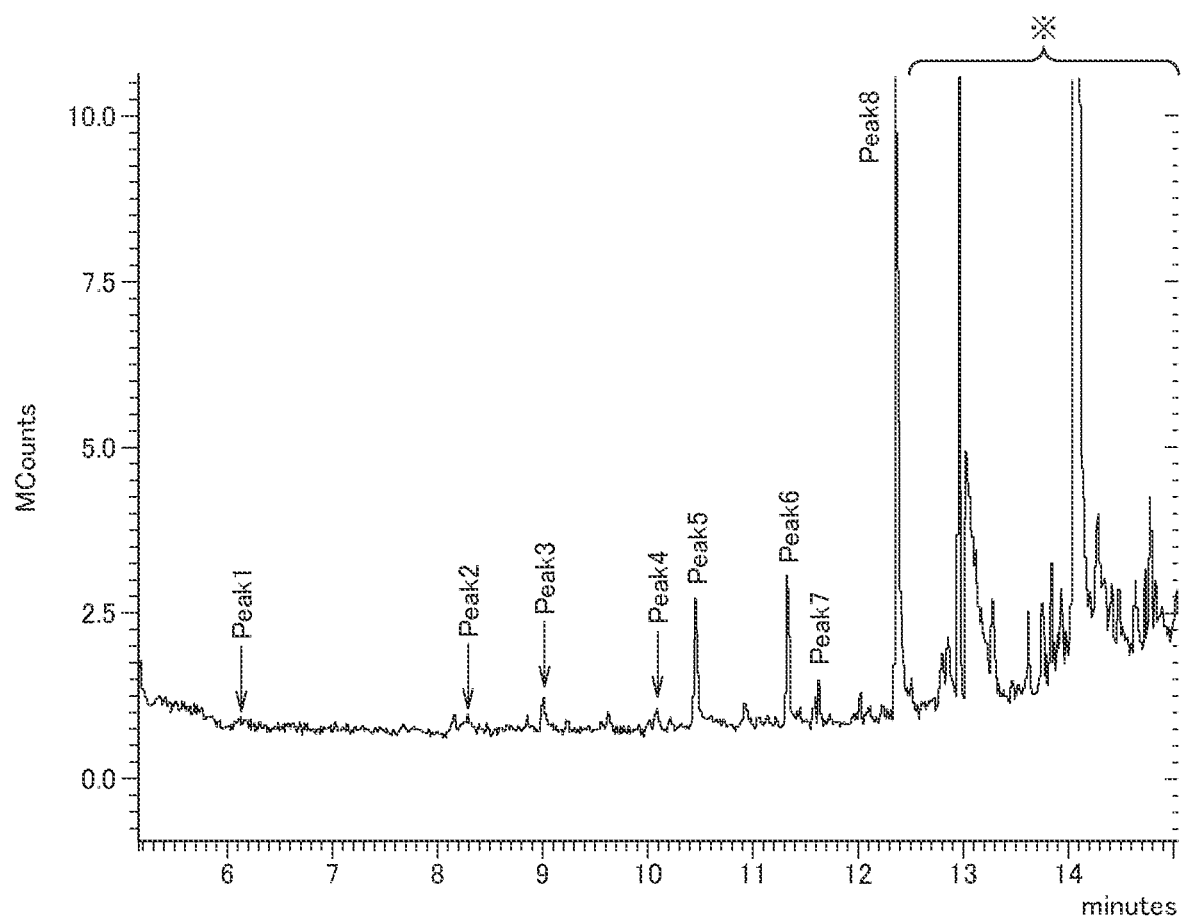
FIG. 1 is a graph illustrating a chart of a gas generated by thermal deterioration of a mineral oil, analyzed with a gas chromatograph-mass spectrometer.
Figure 2:
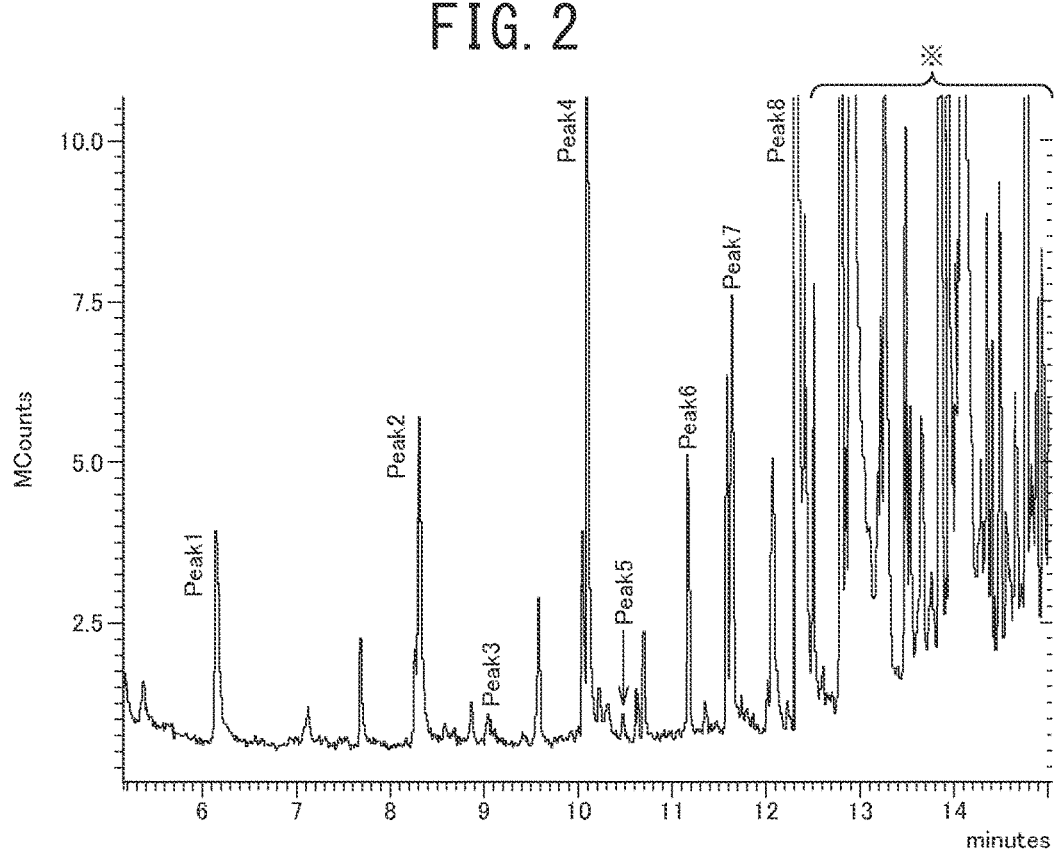
FIG. 2 is a graph illustrating a chart of a gas generated by thermal deterioration of a poly-α-olefin oligomer oil, analyzed with a gas chromatograph-mass spectrometer.
Figure 3:
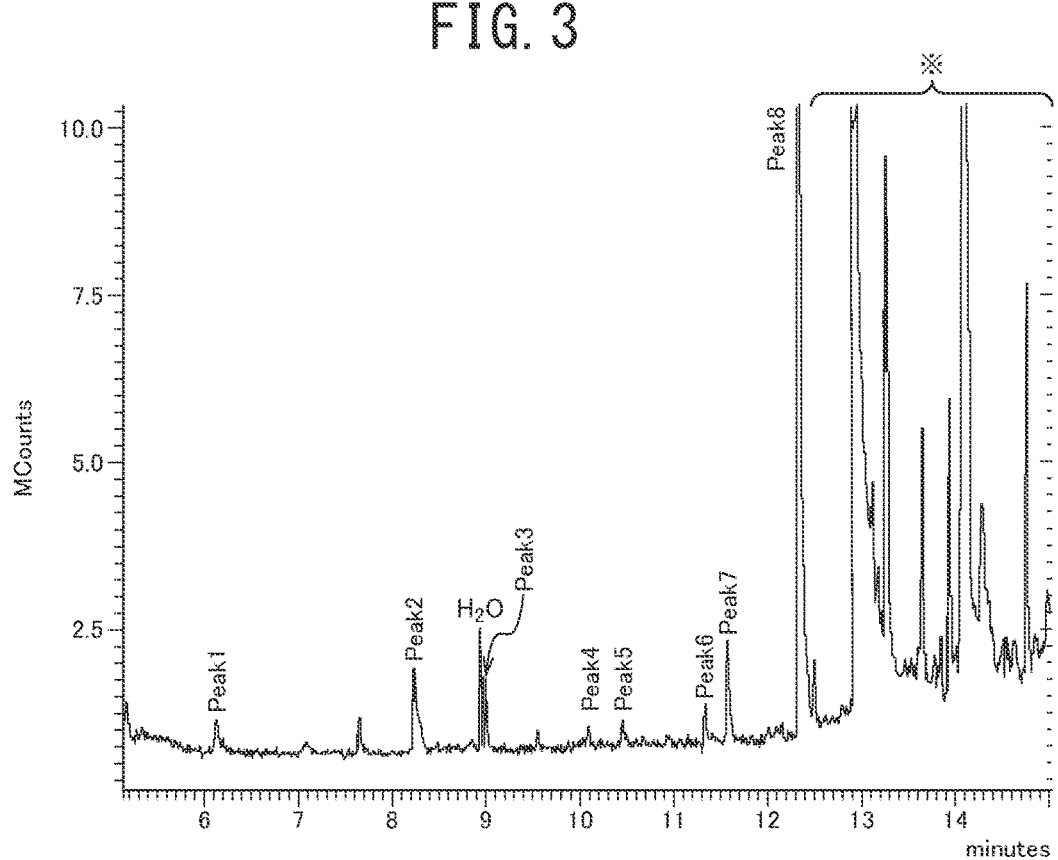
FIG. 3 is a graph illustrating a chart of a gas generated by thermal deterioration of a polyol ester oil, analyzed with a gas chromatograph-mass spectrometer.

FIG. 1 is a chart illustrating the analysis result of the mineral oil, FIG. 2 is a chart illustrating the analysis result of the poly-α-olefin oligomer oil, and FIG. 3 is a chart illustrating the analysis result of the polyol ester oil. Compounds of peaks 1 to 8 in FIG. 1 to FIG. 3 and physical properties thereof are listed in Table 1.

TABLE 1

| No. | Compound name | Type | Molecular weight | Boiling point (° C.) | Vapor pressure at 25° C. (mmHg) |
|---|---|---|---|---|---|
| 1 | n-hexanal | aldehyde | 100.16 | 130 | 15 |
| 2 | n-heptanal | aldehyde | 114.29 | 153 | 3.5 |
| 3 | 6-methyl-2-heptanone | ketone | 128.21 | 173 | 1.6 |
| 4 | octanal | aldehyde | 128.21 | 173 | 1.6 |
| 5 | hydroxyacetic acid | organic acid | 76.05 | 112 | — |
| 6 | hexylhydroxy peroxide | organic peroxide | 118.17 | 112 | — |
| 7 | nonanal | aldehyde | 142.24 | 195 | 0.26 |
| 8 | acetic acid | organic acid | 60.05 | 118 | 20 |

As apparent from FIG. 1 to FIG. 3 and Table 1, different types of lubricants yield common carbonyl compounds (aldehydes, a ketone, an organic peroxide, organic acids) as smelling components. Although this analysis recorded the result from 5 minutes as the elution time, smelling components probably also includes formaldehyde, acetaldehyde, propanal, butanal, pentanal, formic acid, and the like, which have lower boiling points than those of the compounds listed in Table 1.

The molecular weights, the boiling points, and the vapor pressures of formaldehyde, acetaldehyde, propanal, butanal, pentanal, and formic acid are listed in Table 2.

TABLE 2

| Compound name | Type | Molecular weight | Boiling point (° C.) | Vapor pressure at 20° C. (mmHg) |
|---|---|---|---|---|
| formaldehyde | aldehyde | 30.03 | −20 | 760 |
| acetaldehyde | aldehyde | 44.05 | 20 | 754.5 |
| propanal | aldehyde | 58.08 | 49 | 234.8 |

TABLE 2-continued

| Compound name | Type | Molecular weight | Boiling point (° C.) | Vapor pressure at 20° C. (mmHg) |
|---|---|---|---|---|
| butanal | aldehyde | 72.11 | 75 | 90.00 |
| pentanal | aldehyde | 86.13 | 103 | 26.25 |
| formic acid | organic acid | 46.025 | 100 | 34.50 |

Such low-molecular weight carbonyl compounds have low boiling points of 118° C. to 195° C., usually have high vapor pressures, easily volatilize when a lubricant deteriorates, thus are easily collected, and are preferred as components for examining lubricant deterioration (detection targets). Such highly volatile compounds quickly absorb to/desorb from a detector of a gas sensor (a film formed on the resonator surface in the case a quartz resonator sensor) and are unlikely to be left, resulting in satisfactory responsivity of the gas sensor.

Of the above compounds, formaldehyde, acetaldehyde, propanal, butanal, pentanal, n-hexanal, n-heptanal, formic acid, and acetic acid are particularly preferred as the detection target, in terms of boiling points and vapor pressure values.

Hence, it has been thought that by using a gas sensor capable of highly accurately detecting a minute amount of a carbonyl compound (at least one of formaldehyde, acetaldehyde, propanal, butanal, pentanal, n-hexanal, n-heptanal, formic acid, and acetic acid) as a main smelling component generated by deterioration of a lubricant in a rolling bearing, the determination accuracy of lubricant deterioration can be improved.

Hydrogen sulfide and ammonia as the detection targets of the lubricant deterioration detection device in PTL 1 are gases derived from additive components and are not contained in some lubricants. Hydrocarbons are generated when a rolling bearing is at a high temperature but a lubricant does not deteriorate yet, and thus use of a device of detecting hydrocarbons to determine lubricant deterioration is likely to lead to an incorrect result.

First Embodiment

An embodiment in a first aspect of the present invention will now be described, but the invention is not limited to the following embodiment. The following embodiment includes technically preferred limitations for carrying out the invention, but the limitations are not essential requirements of the invention.

<Structure of Lubricant Deterioration Detection Device>

Figure 4:
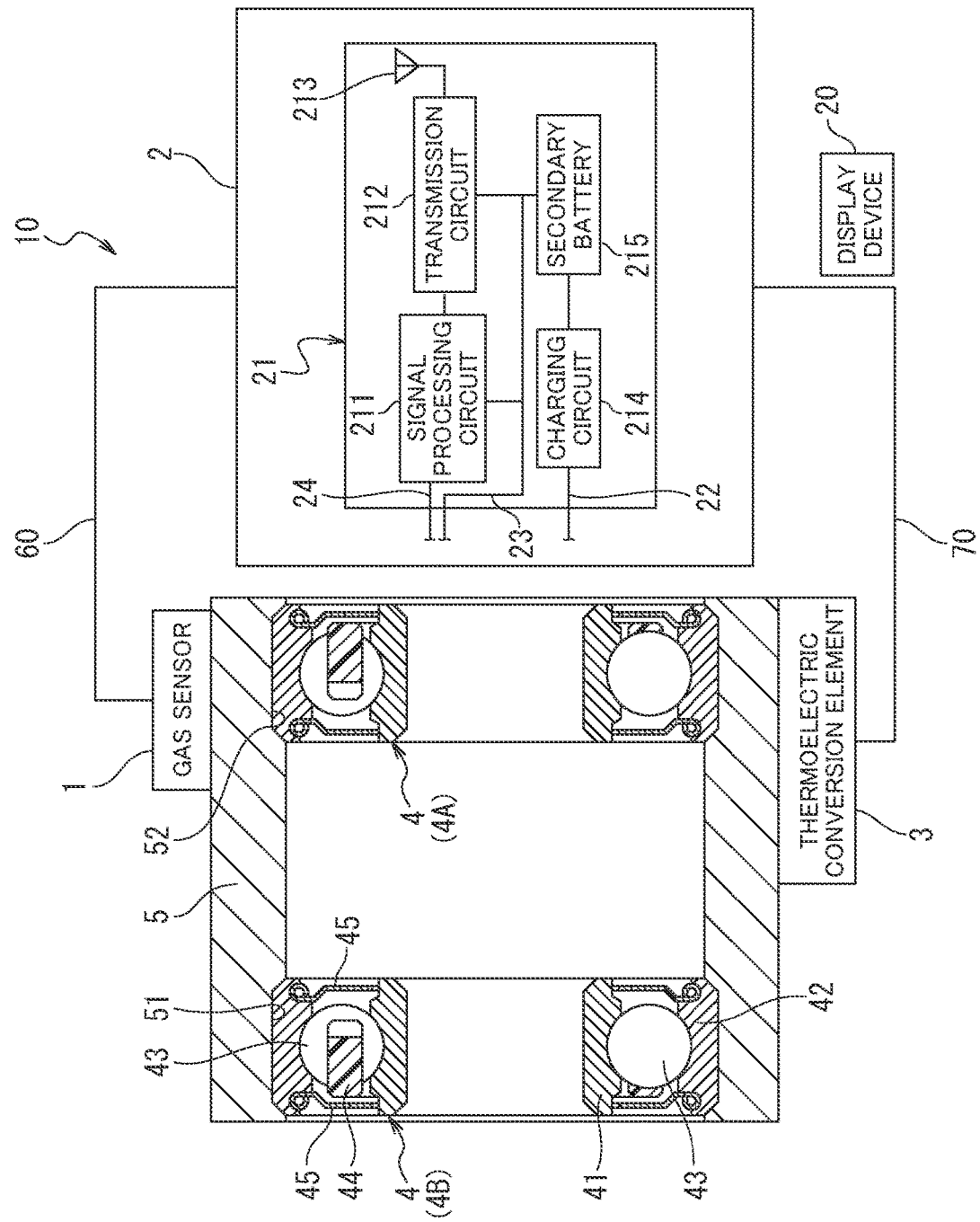
FIG. 4 is a view illustrating a lubricant deterioration detection device of a first embodiment attached to a cylinder to which outer rings of rolling bearings are fixed.

As illustrated in FIG. 4, a lubricant deterioration detection device 10 in the present embodiment includes a gas sensor 1, a radio transmitter 2, a display device (receiver) 20, and a thermoelectric conversion element 3. The gas sensor 1, the radio transmitter 2, and the thermoelectric conversion element 3 are fixed onto the outer peripheral surface of a cylinder 5. The cylinder 5 is a bearing housing in which outer rings of rolling bearings are fitted. To the cylinder 5, two identical rolling bearings 4 are attached.

The rolling bearings 4 (4A, 4B) are sealed deep groove ball bearings each including an inner ring 41, an outer ring 42, balls 43, a retainer 44, and shield plates 45. At both axial ends on the inner peripheral surface of the cylinder 5, grooves 51, 52 are formed for fitting the outer rings 42 of the rolling bearings 4A, 4B.

The gas sensor 1, the radio transmitter 2, and the thermoelectric conversion element 3 are located on the cylinder 5 at positions where the outer ring 42 of the rolling bearing 4A is fixed in the axis direction. The gas sensor 1, the radio transmitter 2, and the thermoelectric conversion element 3 are located on the cylinder 5 at positions different in the circumferential direction. The gas sensor 1 and the radio transmitter 2 are connected through a wiring 60, and the radio transmitter 2 and the thermoelectric conversion element 3 are connected through a wiring 70. The display device 20 is located at a position apart from the cylinder 5.

Figure 5:
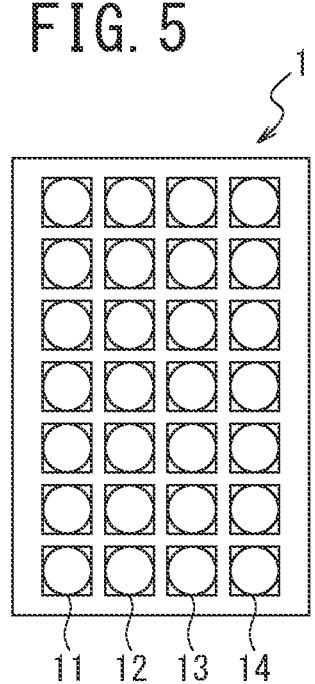
FIG. 5 is a schematic view illustrating a gas sensor included in the lubricant deterioration detection device of the first embodiment.

As the gas sensor 1, a micro gas sensor array produced by MEMS (micro electro mechanical systems) technology can be used, for example. An example of the micro gas sensor array is illustrated in FIG. 5. The micro gas sensor array in FIG. 5 includes seven rows each including four channels 11 to 14. The number of rows can be optional. A larger number of rows can improve detection sensitivity. The first channel 11 selectively detects n-hexanal and n-heptanal. The second channel 12 selectively detects hydrocarbons. The third channel 13 selectively detects water. The fourth channel 14 selectively detects oxygen.

As each sensor included in the micro gas sensor array, a quartz resonator sensor can be used. In the case, for example, a film of polyethylene glycol 2000 is formed on the resonator surface in the first channel 11. In the second channel 12, for example, a polyvinyl chloride (PVC) film is formed on the resonator surface.

In the third channel 13, for example, a poly(3,4-ethylenedioxythiophene)/poly(styrenesulfonate) (PEDOT/PSS: polythiophene-based electrically conductive polymer) film is formed on the resonator surface. In the fourth channel 14, for example, a tin oxide ($SnO_2$) film is formed on the resonator surface. Each film can be formed by spin coating or sputtering, and the film thickness is preferably 50 nm, for example.

As the radio transmitter 2, a radio transmitter including a circuit board 21 can be used, for example. In the case, the circuit board 21 includes a signal processing circuit 211, a transmission circuit 212, an antenna 213, a charging circuit 214, and a secondary battery 215. An input power line 22 of the radio transmitter 2 is connected through the wiring 70 to the thermoelectric conversion element 3. An output power line 23 and an input signal processing line 24 of the radio transmitter 2 are connected through the wiring 60 to the gas sensor 1.

Figure 6:
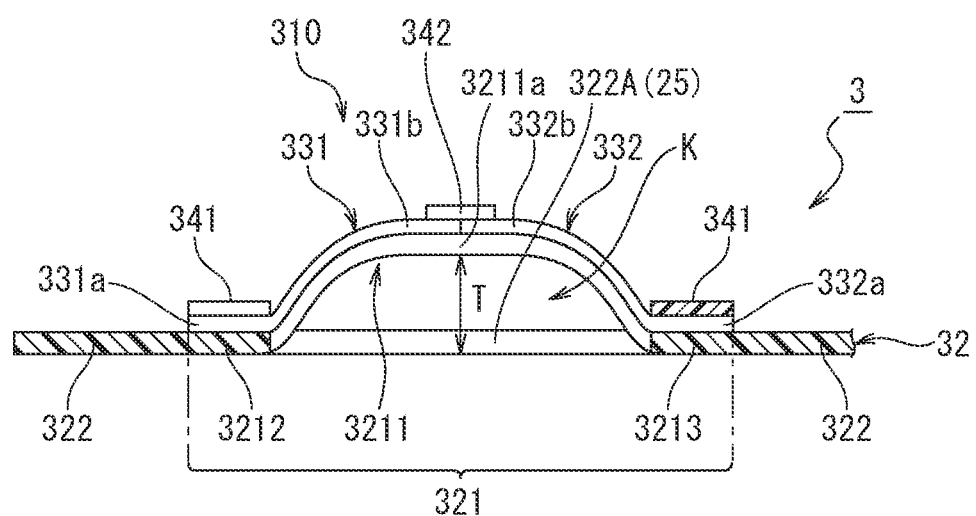
FIG. 6 is a partial cross-sectional view illustrating a thermoelectric conversion element included in the lubricant deterioration detection device of the first embodiment and illustrates a unit formation portion of a substrate corresponding to a single thermoelectric conversion unit and non-formation portions on the respective sides thereof.
Figure 7:
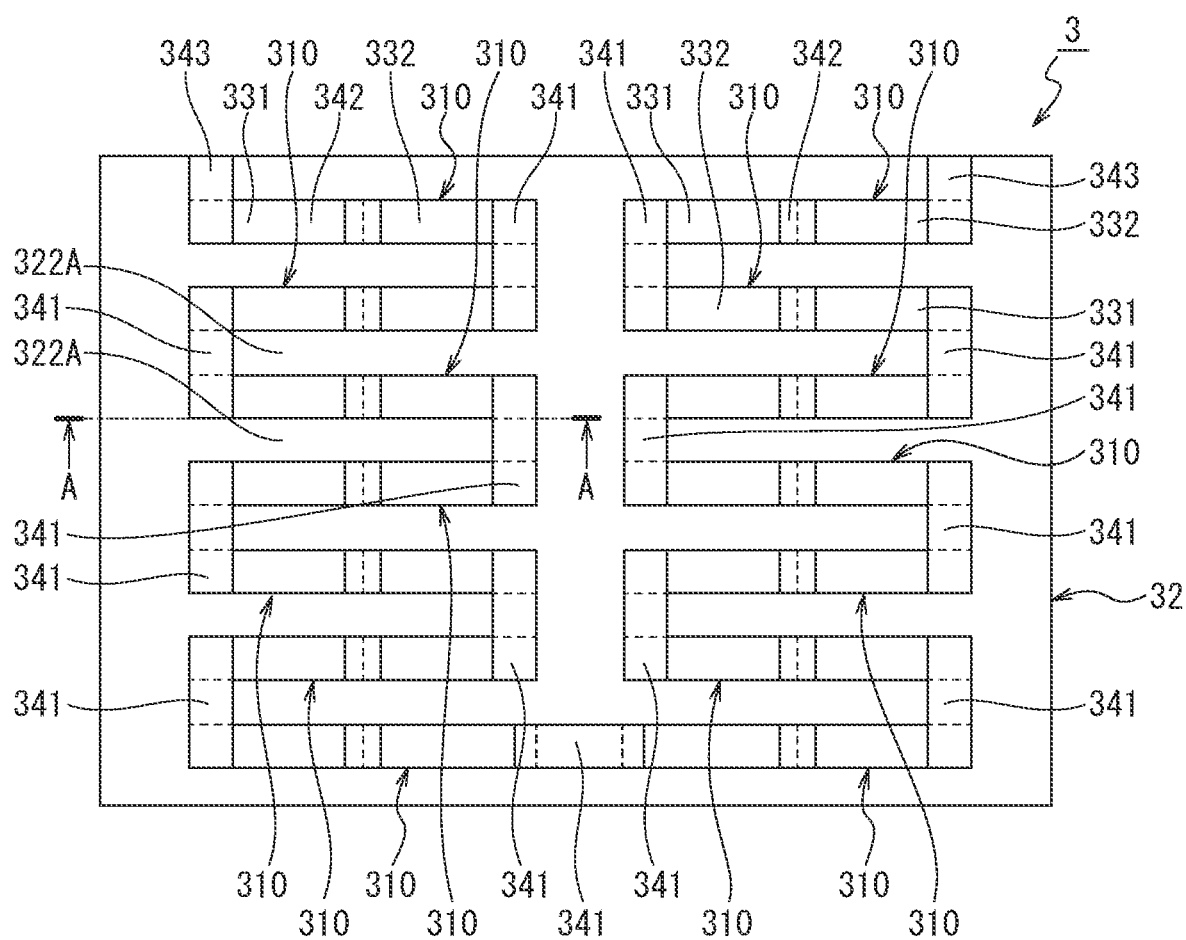
FIG. 7 is a plan view illustrating the state before a projection forming step (after a second print step) of the thermoelectric conversion element included in the lubricant deterioration detection device of the first embodiment.

As the thermoelectric conversion element 3, a thermoelectric conversion element including a flexible substrate 32 and a plurality of thermoelectric conversion units 310 of a printed pattern formed on the substrate 32 can be used, as illustrated in FIG. 6 and FIG. 7. In the case, a cross-sectional shape of a unit formation portion 321 of the substrate 32 on which a thermoelectric conversion unit 310 is formed includes a projection portion 3211, a first base portion part 3212, and a second base portion 3213. The first base portion 3212 and the second base portion 3213 are located at the respective sides of the projection portion 3211, are lower than the projection portion, and are as high as non-formation portions 322 on which no thermoelectric conversion unit 310 is formed.

In the case, as illustrated in FIG. 6, the thermoelectric conversion unit 310 includes a first layer 331 from the first base portion 3212 of the unit formation portion 321 to a top 3211a of the projection portion 3211 and a second layer 332 from the top 3211a to the second base portion 3213. The unit formation portion 321 is separated in the whole region of the projection portion 3211 from a non-formation portion 322A (see FIG. 7) behind the plane of FIG. 6 (appearing below the projection portion 3211). The first layer 331 is formed from a p-type electrically conductive polymer (thermoelectric conversion material), and the second layer 332 is formed from a cured product of silver paste (electrically conductive material).

As the thermoelectric conversion element 3, a thermoelectric conversion element in which 100 of the thermoelectric conversion units 310 illustrated in FIG. 6 are arranged in a 10×10 matrix can be used. In the case, these thermoelectric conversion units 310 are connected in series. FIG. 7 illustrates a thermoelectric conversion element 3 in which 14 thermoelectric conversion units 310 are formed in two columns and seven rows on a substrate 32, for simple explanation. FIG. 6 is a cross-sectional view taken along the line A-A in FIG. 7.

In the case, lower wirings 341 are formed above the first base portions 3212 and the second base portions 3213 through the first layers 331 and the second layers 332 and each connect a first layer 331 and a second layer 332 of the adjacent thermoelectric conversion units 310.

In the case, the first layer 331 and the second layer 332 are formed from different materials, and thus an upper wiring 342 for connecting the first layer 331 and the second layer 332 in each thermoelectric conversion unit 310 is formed at the top 3211a of the projection portion 3211. The ends of the series connection are located on one edge of the substrate 32, and at each position, an external connection terminal 343 is formed.

In the case, each thermoelectric conversion unit 310 has a height difference between a lower part 331a that is a part of the first layer 331 on the first base portion 3212 or a lower part 332a that is a part of the second layer 332 on the second base portion 3213 and upper parts 331b, 332b of the first layer 331 and the second layer 332 on the top 3211a, and the height difference is not less than the thicknesses of the first layer 331 and the second layer 332.

In the case, the substrate 32 of the thermoelectric conversion element 3 is fixed to the cylinder 5, and the pair of connection terminals 343 of the thermoelectric conversion element 3 are connected through the wiring 70 to the power line 22 of the radio transmitter 2.

<Operation of Lubricant Deterioration Detection Device>

When heat generated by rotation of the rolling bearings 4 heats the cylinder 5, a temperature difference is caused between the lower parts 331a, 332a and the upper parts 331b, 332b of each thermoelectric conversion unit 310 included in the thermoelectric conversion element 3. Accordingly, the thermoelectric conversion element 3 generates electricity, and electric current signals produced by the electricity flow through the power line 22 into the charging circuit 214 on the circuit board 21 and are charged in the secondary battery 215.

The electric current in the secondary battery 215 drives the signal processing circuit 211 and the transmission circuit 212 and is supplied through the power line 23 to the gas sensor 1.

Accordingly, the radio transmitter 2 processes detection data input from the gas sensor 1, with the signal processing circuit 211 and the transmission circuit 212 and transmits the result as radio waves from the antenna 213. The display device 20 receives the detection data transmitted as radio waves from the antenna 213 of the radio transmitter 2 and displays the detection result.

<Sensed Result by Sensor Array and Determination Method>

Figure 8:
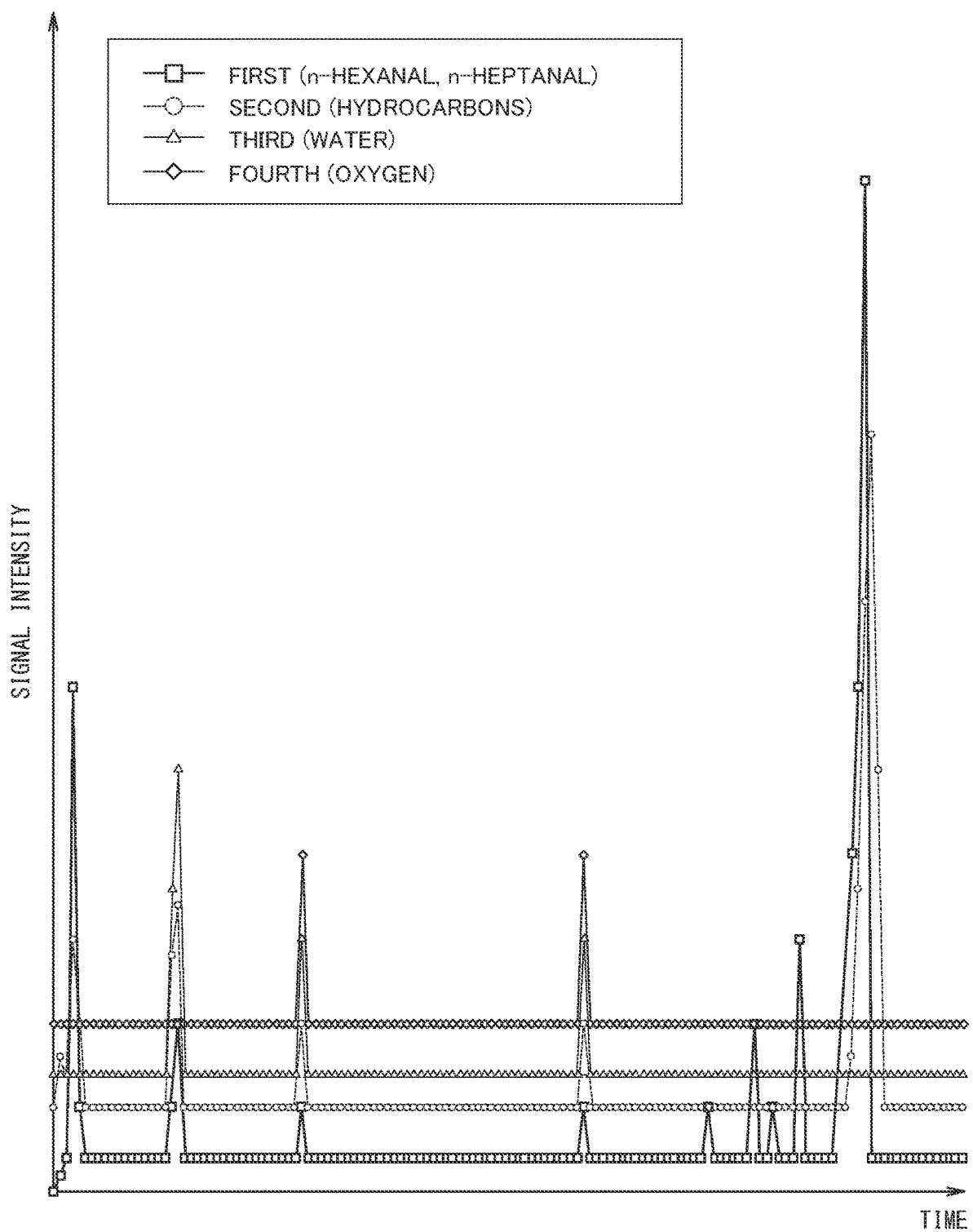
FIG. 8 is a graph illustrative of virtual time courses of component intensities detected by a gas sensor.

A virtual example prepared for explanation of a determination method using the sensor array is illustrated in FIG. 8. The case in which a peak of the first channel (n-hexanal and n-heptanal) 11 and a peak of the second channel (hydrocarbons) 12 are observed at the initial state of rotation will be described. In this case, the peaks are supposed to be formed in the process in which a lubricant is widely spread in and fits with the whole bearing at the initial state of rotation. In other words, at this time point, n-hexanal and/or n-heptanal produced by decomposition of a lubricant that is being spread in the whole bearing and hydrocarbons produced by evaporation of low-molecular weight substances contained in the lubricant in association with a temperature increase are considered to be detected.

The case in which a peak of the first channel 11, a peak of the second channel 12, and a peak of the third channel (water) 13 are subsequently observed will be described. In this case, air (air in the space where the tester is installed) enters a sensor attachment position at this time point, and n-hexanal and/or n-heptanal, hydrocarbons, and water contained in the air are considered to be detected.

The case in which peaks of the first channel 11 and the second channel 12 and peaks of the third channel 13 and the fourth channel (oxygen) 14 are subsequently observed will be described. In this case, exhaust gas from gasoline-fueled cars or the like passing near the tester enters a sensor attachment position at this time point, and oxygen, water, hydrocarbons, and n-hexanal and/or n-heptanal contained in the exhaust gas are considered to be detected.

The case in which only a peak of the first channel 11 is subsequently observed just before seizing up will be described. From the case, detection of only the peak of the first channel 11, or detection of only n-hexanal and/or n-heptanal can be considered to indicate a prediction of seizing up. Hence, if the rotation of a bearing is stopped upon this detection, the breakage of a bearing due to seizing up or damage to other devices can be minimized, and the operation of an apparatus can be safety stopped.

<Effect of Lubricant Deterioration Detection Device>

The lubricant deterioration detection device disclosed in PTL 1 uses a gas sensor that detects at least any gas of hydrocarbons, hydrogen sulfide, and ammonia, whereas the lubricant deterioration detection device in the present embodiment can use a gas sensor 1 that includes a highly sensitive micro gas sensor array prepared by MEMS technology and includes a plurality of channels including a channel for detecting n-hexanal and n-heptanal (first channel 11).

Detection of hydrocarbons indicates evaporation of low-molecular weight substances in association with a temperature increase of a lubricant but does not directly indicate lubricant deterioration.

Hence, the lubricant deterioration detection device of the embodiment should improve the determination accuracy of lubricant deterioration as compared with the lubricant deterioration detection device disclosed in PTL 1.

To attach the lubricant deterioration detection device disclosed in PTL 1 to a rolling bearing, an opening is formed on a circular plate of a shield plate, and a detector including a gas sensor is attached to the opening. The detector and the device main body (display device) are connected through a wiring. In contrast, in the lubricant deterioration detection device of the embodiment, the gas sensor 1, the radio transmitter 2, and the thermoelectric conversion element 3 are fixed onto the outer peripheral surface of the cylinder 5, and the detection result is displayed on the display device 20 wirelessly connected to the gas sensor 1.

In other words, the lubricant deterioration detection device of the embodiment neither damages the rolling bearings 4 nor has any wiring extending from the rolling bearings 4 to the display device 20. Lubricant deterioration can be continuously monitored on the display device 20 located apart from the rolling bearings 4.

<Method for Producing Thermoelectric Conversion Element>

A method for producing the thermoelectric conversion element 3 will be described with a thermoelectric conversion element including 14 thermoelectric conversion units 310 in two columns and seven rows.

Figure 9:
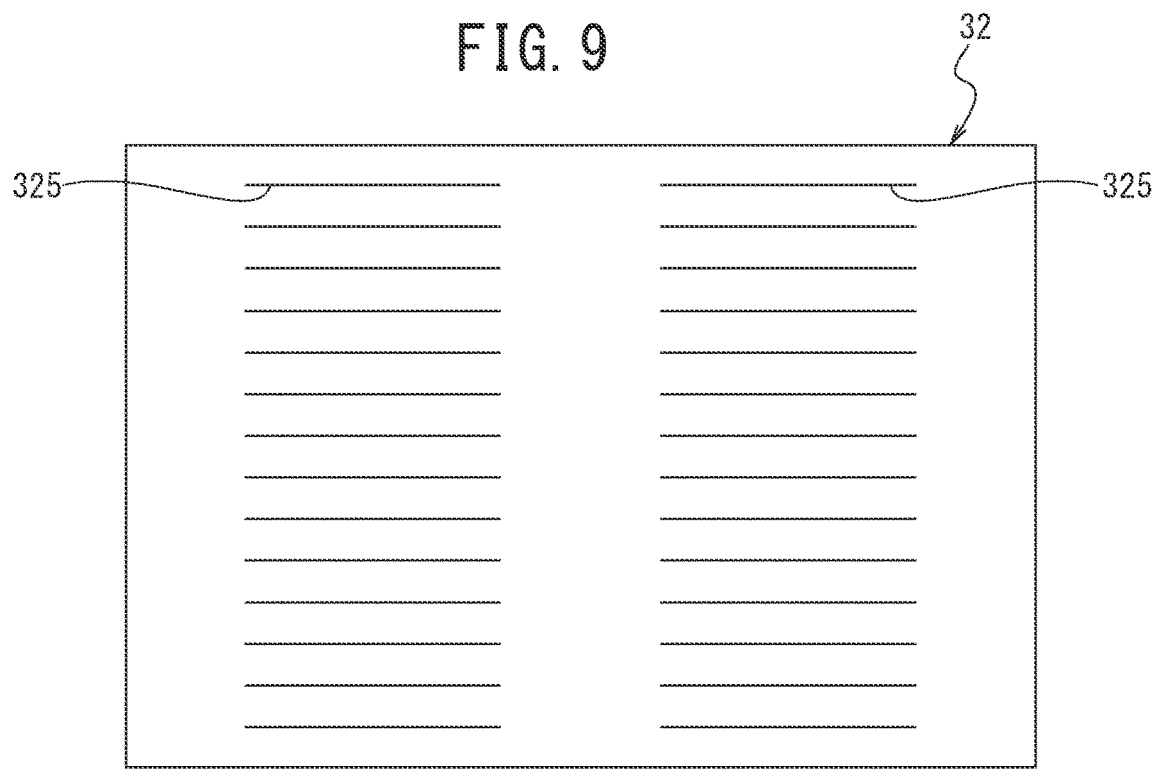
FIG. 9 is a plan view illustrative of a slit forming step included in a method for producing the thermoelectric conversion element illustrated in FIG. 6.
Figure 10:
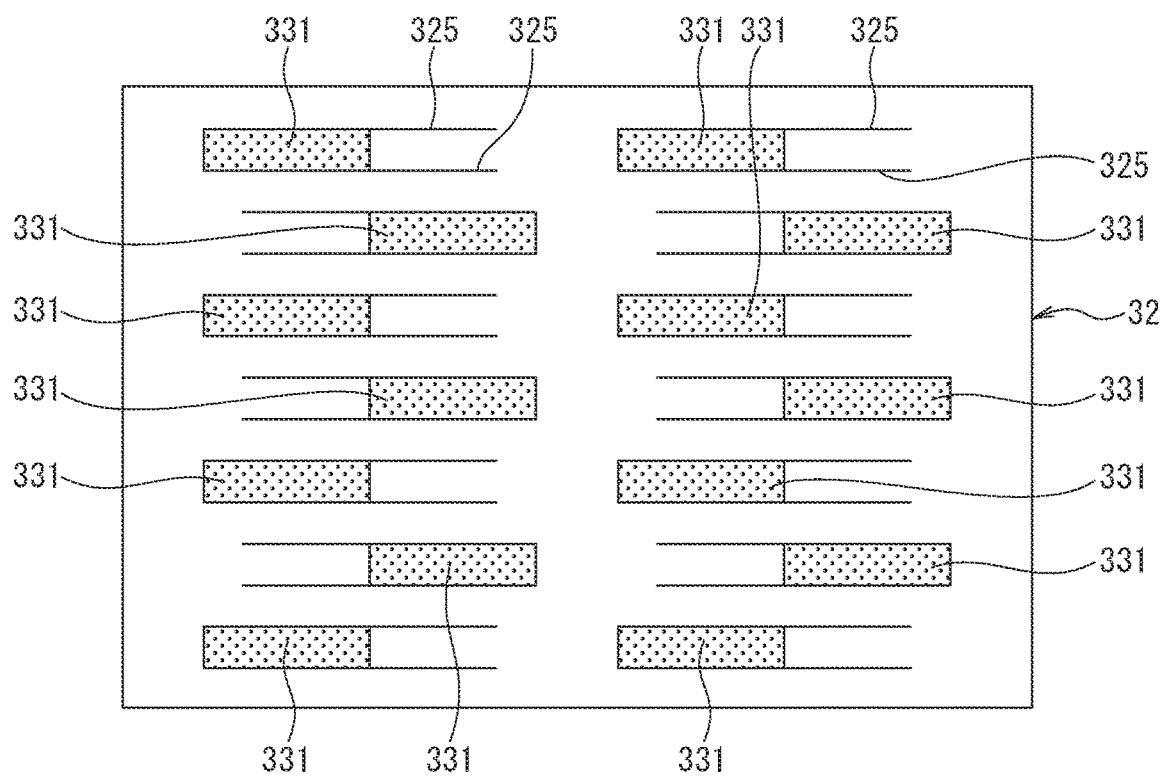
FIG. 10 is a plan view illustrative of a former step in a first print step included in the method for producing the thermoelectric conversion element illustrated in FIG. 6.
Figure 11:
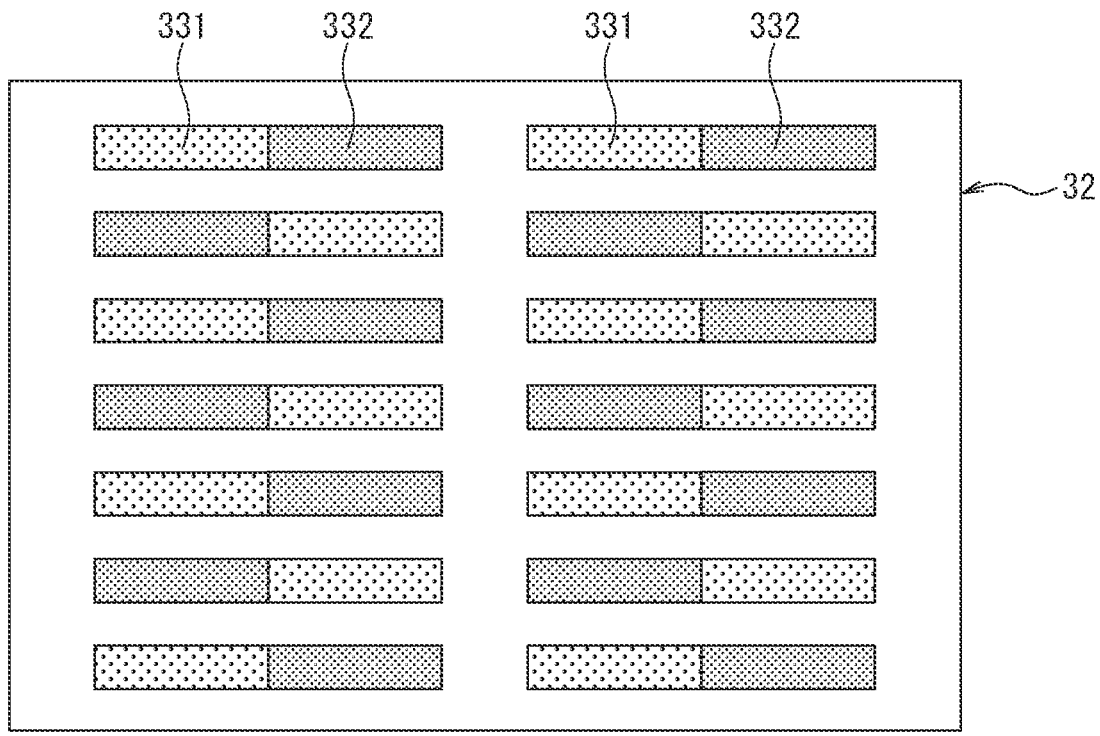
FIG. 11 is a plan view illustrative of a latter step in the first print step included in the method for producing the thermoelectric conversion element illustrated in FIG. 6.
Figure 12:
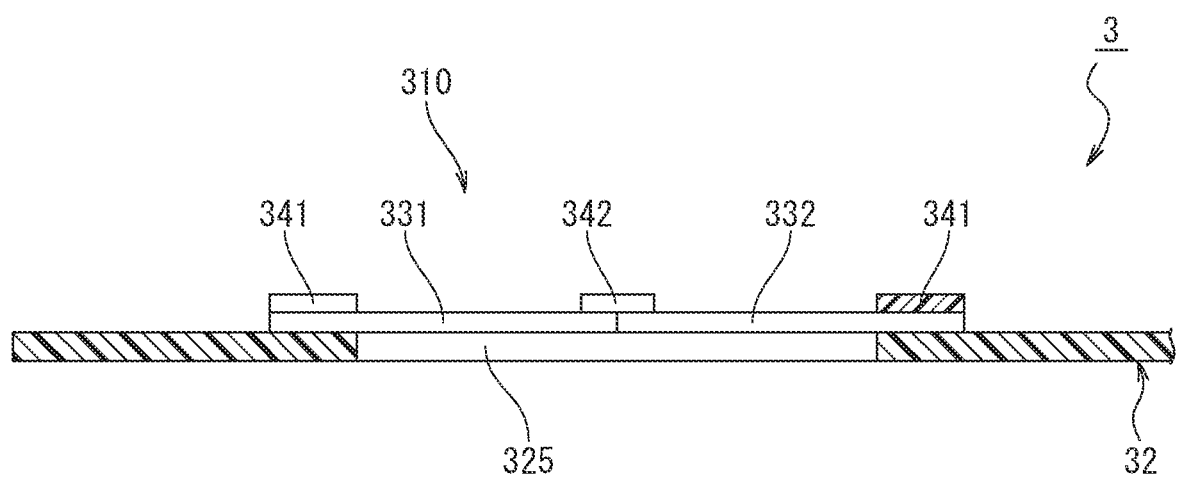
FIG. 12 is a cross-sectional view taken along the line A-A in FIG. 7.

The thermoelectric conversion element 3 is produced by performing a slit forming step illustrated in FIG. 9, a former step in a first print step illustrated in FIG. 10, a latter step in the first print step illustrated in FIG. 11, a second print step illustrated in FIG. 7, and a projection forming step of making the state in FIG. 12 into the state in FIG. 6, in this order.

In the method for producing the thermoelectric conversion element 3 in the embodiment, 28 slits 325 corresponding to 14 thermoelectric conversion units 310 illustrated in FIG. 7 are first formed on a substrate 32, as illustrated in FIG. 9. The slits 325 are formed to have the same length as the formation distance of a pair of lower wirings 341 in a thermoelectric conversion unit 310. In other words, slits 325 are formed in the entire region of the substrate 32 in which projection portions 3211 are formed.

Next, as the former step in the first print step, a first layer 331 is formed for each thermoelectric conversion unit 310 in the width between two adjacent slits 325 in each column, as illustrated in FIG. 10. Adjacent first layers 331 in a column or between columns of 14 thermoelectric conversion units 310 in the two columns are provided at opposite positions in the length direction of the slits 325. An end of each first layer 331 along the slits 325 protrudes outward from the slits 325.

Next, as the latter step in the first print step, a second layer 332 is formed for each thermoelectric conversion unit 310 in the width between two adjacent slits 325 in each column, as illustrated in FIG. 11. The second layer 332 is formed in contact with the adjacent first layer 331 to have the same thickness as that of the first layer 331.

Through the process, a thermoelectric conversion pattern including all the first layers 331 and the second layers 332 constituting 14 thermoelectric conversion units 310 in two columns are formed on the substrate 32. In the state of FIG. 11, the portions including the first layers 331 and the second layers 332 on the substrate 32 are unit formation portions, and the other portions are non-formation portions.

Next, as the second print step, a conductive layer pattern including lower wirings 341, connection terminals 343, and upper wirings 342 is formed as illustrated in FIG. 7, on the thermoelectric conversion pattern illustrated in FIG. 11. The thermoelectric conversion units 310 in the state are formed in a planar shape on the planar substrate 32, as illustrated in FIG. 12.

Next, as the projection forming step, a mold having male portions corresponding to the projection portion 3211 in FIG. 6 is pressed against the back face of the substrate 32 where the slits 325 are formed (face without the thermoelectric conversion units 310). This pressing draws and deforms the first layers 331, the second layers 332, and portions of the substrate 32 with the first layers 331 and the second layers 332, forming projection portions 3211. For the pressing, a mold having male portions corresponding to the projection portions 3211 of all the unit formation portions 321 is used to form the projection portions 3211 for all the thermoelectric conversion units 310 at once.

In the thermoelectric conversion element 3 produced in this manner, each thermoelectric conversion unit 310 has a height difference between the lower part 331a that is a part of the first layer 331 on the first base portion 3212 or the lower part 332a that is a part of the second layer 332 on the second base portion 3213 and the upper parts 331b, 332b of the first layer 331 and the second layer 332 on the top 3211a, and the height difference is not less than the thicknesses of the first layer 331 and the second layer 332.

Hence, even when the thermoelectric conversion element 3 is placed on a planar heating element (for example, a hot plate) while the non-formation portion 322 of the substrate 32 is horizontally held and the lower parts 331a of the first layers 331 and the lower parts 332a of the second layers 332 are heated through the substrate 32, high electric power generation performance can be achieved. In addition, the substrate 32 with the printed pattern can be simply, stably installed on a heating element.

The whole region of the projection portion 3211 in each unit formation portion 321 is separated from non-formation portions 322A. Lower spaces K of the projection portions 3211 thus continue to form an air flow path in each column of the thermoelectric conversion units 310. Hence, by flowing air through the flow paths including the lower spaces K to cool the tops 3211a at the time of heating of the substrate 32, a larger temperature difference can be produced between the lower parts 331a, 332a and the upper parts 331b, 332b of the thermoelectric conversion units 310.

[Selective Adsorption Film of Gas Sensor]

<Sensor Selectively Detecting n-Hexanal, n-Heptanal>

Examples of the material of the film selectively adsorbing at least one of n-hexanal and n-heptanal include polynaphthylamine, high-density polyethylene, EVOH (ethylene-vinyl alcohol copolymer), dinitrophenylhydrazine, nitroterephthalic acid-modified polyethylene glycol, polyethyleneimine, and ABS resins, in addition to the above polyethylene glycol.

When a polynaphthylamine film is compared with a polyethylene glycol film as the film formed on the resonator surface of a quartz resonator sensor, the quartz resonator sensor using the polyethylene glycol film achieves higher sensitivity of detecting n-hexanal and n-heptanal than that using the polynaphthylamine film. Hence, the polyethylene glycol film is preferably used.

<Sensor Selectively Detecting Low-Molecular Weight Carbonyl Compounds>

Examples of the film selectively adsorbing formaldehyde, acetaldehyde, propanal, butanal, pentanal, n-hexanal, n-heptanal, formic acid, and acetic acid as low-molecular weight carbonyl compounds include polynaphthylamine, high-density polyethylene, polyethylene glycol, EVOH (ethylene-vinyl alcohol copolymer), dinitrophenylhydrazine, nitroterephthalic acid-modified polyethylene glycol, polyethyleneimine, and ABS resins.

When a method using molecular template technology is used to form a selective adsorption film for a carbonyl compound on a quartz crystal microblance (QCM) sensor, a strain sensor, a pressure sensor, or the like, a sensor having higher selectivity can be prepared.

As an example, a selective adsorption film for acetic acid was prepared by molecular template technology, and the performance of the sensor was examined. Specifically, a polymer thin film selectively adsorbing acetic acid was formed on a quartz crystal microblance (QCM) sensor by the following procedure.

First, 1.44 g of tertiary-butyl methacrylate and 1.98 g of ethylene glycol dimethacrylate were placed in a container, then, 0.22 g of acetic acid was added into the container, and 0.18 g of 1-hydroxycyclohexyl phenyl ketone as a radical generator and 10 ml of chloroform were further added, giving a monomer solution. With a micropipette, 0.5 µl of the monomer solution was taken and dropped on a round blank of a QCM (nominal frequency: 9 MHz) sensor manufactured by Nihon Dempa Kogyo Co., Ltd.

Next, to the liquid film on the blank formed by the dropping, ultraviolet light was applied at only an integrated light quantity of 4,200 mJ to cure the liquid film. Next, the cured film was washed with water, warm water, and distilled water to elute acetic acid from the film, and the resulting film was dried. Consequently, a polymer thin film having the template of acetic acid was formed on the QCM sensor.

Figure 13:
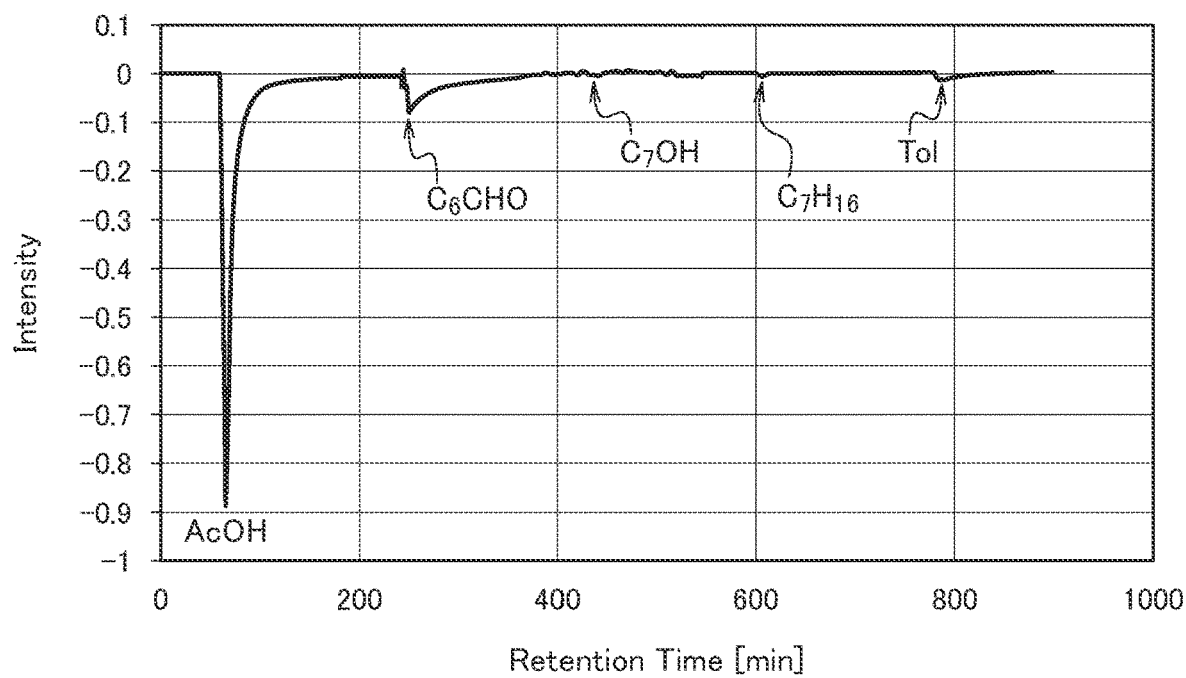
FIG. 13 is a graph illustrating the intensities of smelling components measured by bringing a QCM sensor having an acetic acid-selective film into contact with a gas containing acetic acid (AcOH), n-heptanal ($C_6CHO$), n-heptanol ($C_7OH$), n-heptane ($C_7H_{16}$), and toluene (Tol) as the smelling components.

The resulting QCM sensor having the acetic acid-selective film was attached to a QCM measurement apparatus "NAPICOS twin sensor system" manufactured by Nihon Dempa Kogyo Co., Ltd., and was brought into contact with gases each containing 1 ppm acetic acid (AcOH), n-heptanal ($C_6CHO$), n-heptanol ($C_7OH$), n-heptane ($C_7H_{16}$), or toluene (Tol), in this order, determining relative detection intensities. Subsequently, the effect by water was eliminated. The result is illustrated in FIG. 13. As illustrated in FIG. 13, a gas containing acetic acid showed a phenomenon in which acetic acid was adsorbed by the film on the QCM sensor to greatly reduce the oscillating frequency. Gases containing the compounds other than acetic acid hardly changed the oscillating frequency, and this indicates that the compounds other than acetic acid were not adsorbed by the film on the QCM sensor.

Figure 14:
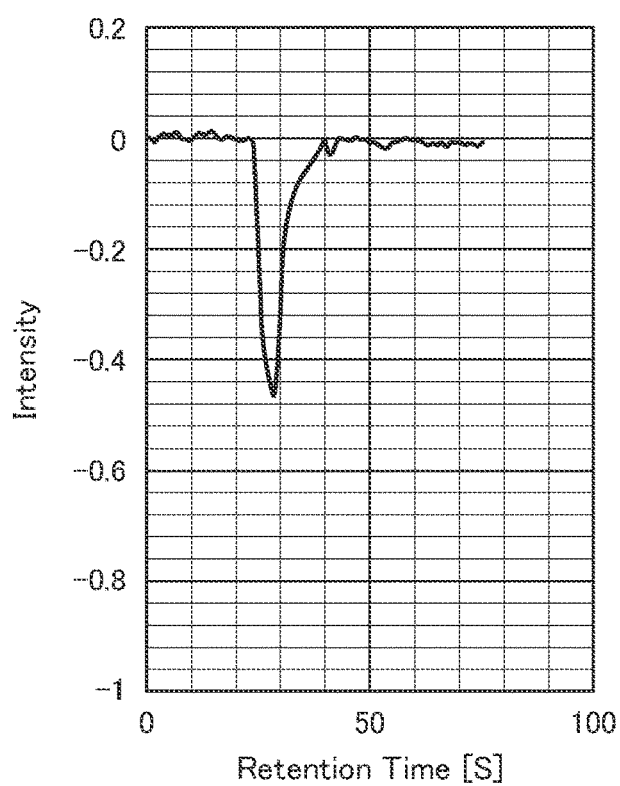
FIG. 14 is a graph illustrating the intensity of acetic acid measured by bringing a QCM sensor having an acetic acid-selective film into contact with a gas generated by thermal deterioration of a poly-α-olefin oligomer oil.

Next, the QCM sensor having the acetic acid-selective film was attached to a QCM measurement apparatus "NAPICOS twin sensor system" and was brought into contact with a gas generated by thermal deterioration of a poly-α-olefin oligomer oil at 120° C. for 1,500 hours, determining the detection intensity of acetic acid. The result is illustrated in FIG. 14. FIG. 14 illustrates that use of the QCM sensor enables detection of acetic acid from smelling components of an oil after thermal deterioration to determine lubricant deterioration.

The smell generated by the thermal deterioration was such a degree as to be slightly sensed by a human, but quantitative determination with a prepared calibration curve revealed that the acetic acid concentration was 500 ppb. Acetic acid at the concentration can be detected at a certain position apart from the machine lubrication position lubricated by a lubricant, and thus the QCM sensor is thought to have acetic acid detection performance for practical use.

Selective adsorption films for carbonyl compounds other than acetic acid can also be prepared by the above procedure using corresponding carbonyl compounds in place of acetic acid.

Preferred Embodiment

The lubricant deterioration detection device in the first aspect of the present invention includes a gas sensor configured to detect a carbonyl compound. The carbonyl compound to be detected is preferably at least one of formaldehyde, acetaldehyde, propanal, butanal, pentanal, n-hexanal, n-heptanal, formic acid, and acetic acid. The gas sensor preferably has a plurality of channels including a channel that selectively detects a carbonyl compound.

An example of the lubricant deterioration detection device in the first aspect of the invention is a lubricant deterioration detection device further including a radio transmitter that wirelessly transmits a detection result by the gas sensor to a receiver and a stand-alone power supply that includes a thermoelectric conversion element and supplies electric power to the gas sensor and the radio transmitter.

The thermoelectric conversion element included in the stand-alone power supply preferably has the following structures (a) to (d) or (a) to (e).

(a) A substrate and a plurality of thermoelectric conversion units formed on the substrate are included.

(b) A cross-sectional shape of a unit formation portion with each thermoelectric conversion unit on the substrate includes a projection portion, a first base portion, and a second base portion, the first base portion and the second base portion are located at the respective sides of the projection portion and are lower than the projection portion, and a non-formation portion without the thermoelectric conversion unit on the substrate is at a lower position than the top of the projection.

(c) The thermoelectric conversion unit includes a first layer from the first base portion of the unit formation portion to the top of the projection portion and a second layer from the top to the second base portion. At least one of the first layer and the second layer is formed from a thermoelectric conversion material. The first layer and the second layer are formed from the same material or different materials. The plurality of thermoelectric conversion units are connected in series.

(d) Lower wirings are formed above the first base portion and the second base portion and each connect the first layer and the second layer of the adjacent thermoelectric conversion units. When the first layers and the second layers are formed from different materials, an upper wiring connecting the first layer and the second layer in each thermoelectric conversion unit is formed at the top. External connection terminals are provided at the respective ends of the series connection.

(e) Each unit formation portion is separated in the region of the projection from the non-formation portion.

Second Aspect

[Discussion by Inventors]

The lubricant deterioration detection device disclosed in PTL 1 includes a gas sensor that detects at least any gas of hydrocarbons, hydrogen sulfide, and ammonia in a bearing.

Figure 15:
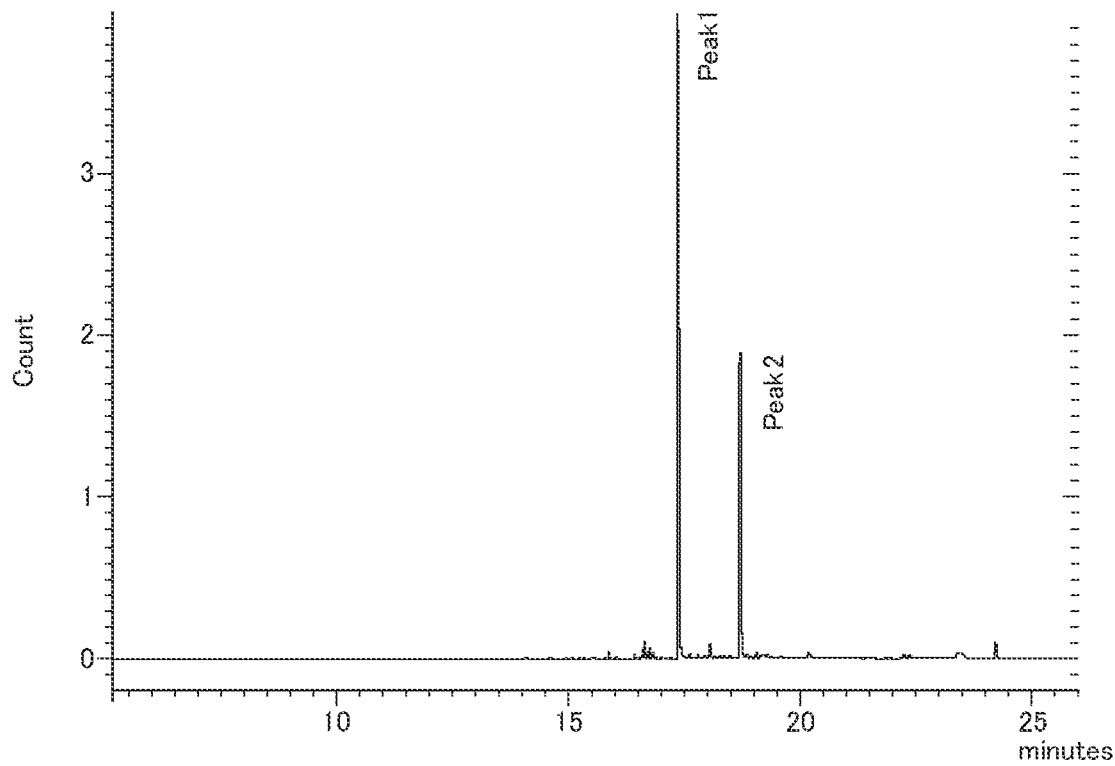
FIG. 15 is a graph illustrating a chart of a smelling gas generated from a rolling bearing immediately before seizing up, analyzed with a gas chromatograph.

However, the inventors of the application have performed a rotation test of a rolling bearing to analyze gases generated from the rolling bearing immediately before seizing up, with a gas chromatograph and have revealed that the main components of the smelling components were n-hexanal and n-heptanal and the concentrations thereof were several tens of parts per million. FIG. 15 is a chart illustrating the analysis result with a gas chromatograph. In FIG. 15, it was ascertained that the peak 1 was n-hexanal and the peak 2 was n-heptanal.

Specifically, the rotation test was performed by continuously rotating a deep groove ball bearing with an inner diameter of 50 mm, an outer diameter of 110 mm, and a width of 27 mm and including noncontact seals in conditions of inner ring rotation, grease lubrication, a rotation speed of 10,000 rpm, and an axial load of 98 N, until seizing up was caused. The grease used was a commercially available grease containing lithium soap as a thickener and mineral oil as a base oil.

In other words, the inventors of the present application have found that n-hexanal and n-heptanal are components predicting lubricant deterioration.

n-Hexanal, which have a boiling point of 130° C., and n-heptanal, which have a boiling point of 152° C., are highly volatile components of the smelling components in a grease after deterioration and thus can be easily collected. Such highly volatile compounds quickly absorb to/desorb from a detector of a gas sensor (a film formed on the resonator surface in the case a quartz resonator sensor) and are unlikely to be left, resulting in satisfactory responsivity of the gas sensor.

Hence, it has been thought that by using a gas sensor capable of highly accurately detecting minute amounts of n-hexanal and/or n-heptanal, which are main smelling components generated by deterioration of a lubricant in a rolling bearing, the determination accuracy of lubricant deterioration can be improved.

Hydrogen sulfide and ammonia as the detection targets of the lubricant deterioration detection device in PTL 1 are gases derived from additive components and are not contained in some lubricants. Hydrocarbons are generated when a rolling bearing is at a high temperature but a lubricant does not deteriorate yet, and thus use of a device of detecting hydrocarbons to determine lubricant deterioration is likely to lead to an incorrect result.

Second Embodiment

An embodiment in a second aspect of the present invention will now be described, but the invention is not limited to the following embodiment. The following embodiment includes technically preferred limitations for carrying out the invention, but the limitations are not essential requirements of the invention.

<Structure of Lubricant Deterioration Detection Device>

Figure 16:
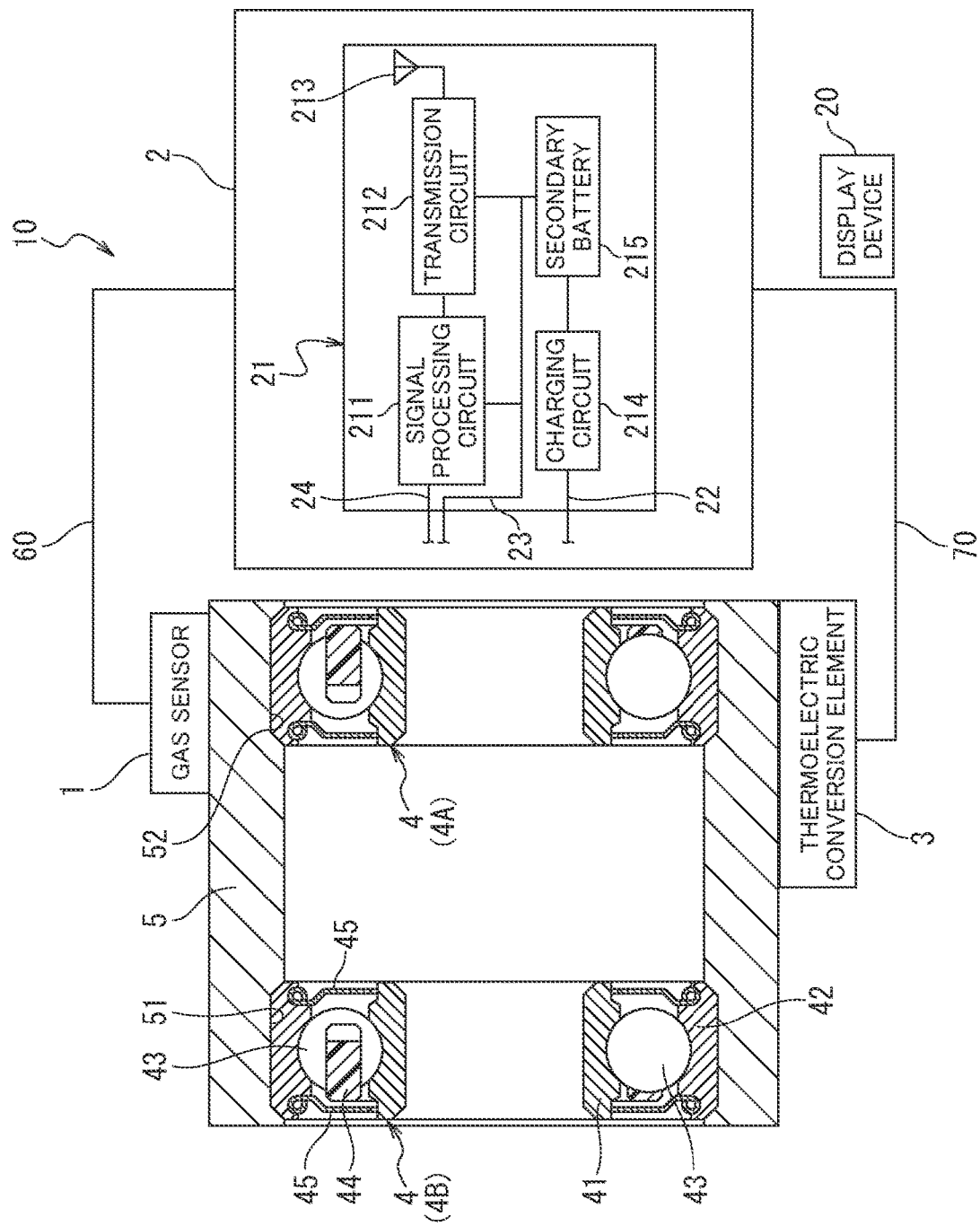
FIG. 16 is a view illustrating a lubricant deterioration detection device of a second embodiment attached to a cylinder to which outer rings of rolling bearings are fixed.

As illustrated in FIG. 16, a lubricant deterioration detection device 10 in the present embodiment includes a gas sensor 1, a radio transmitter 2, a display device (receiver) 20, and a thermoelectric conversion element 3. The gas sensor 1, the radio transmitter 2, and the thermoelectric conversion element 3 are fixed onto the outer peripheral surface of a cylinder 5. The cylinder 5 is a bearing housing in which outer rings of rolling bearings are fitted. To the cylinder 5, two identical rolling bearings 4 are attached.

The rolling bearings 4 (4A, 4B) are sealed deep groove ball bearings each including an inner ring 41, an outer ring 42, balls 43, a retainer 44, and shield plates 45. At the respective axial ends of the cylinder 5 on the inner peripheral surface, grooves 51, 52 are formed for fitting the outer rings 42 of the rolling bearings 4A, 4B.

The gas sensor 1, the radio transmitter 2, and the thermoelectric conversion element 3 are located on the cylinder 5 at positions where the outer ring 42 of the rolling bearing 4A is fixed in the axis direction. The gas sensor 1, the radio transmitter 2, and the thermoelectric conversion element 3 are located on the cylinder 5 at positions different in the circumferential direction. The gas sensor 1 and the radio transmitter 2 are connected through a wiring 60, and the radio transmitter 2 and the thermoelectric conversion element 3 are connected through a wiring 70. The display device 20 is located at a position apart from the cylinder 5.

Figure 17:
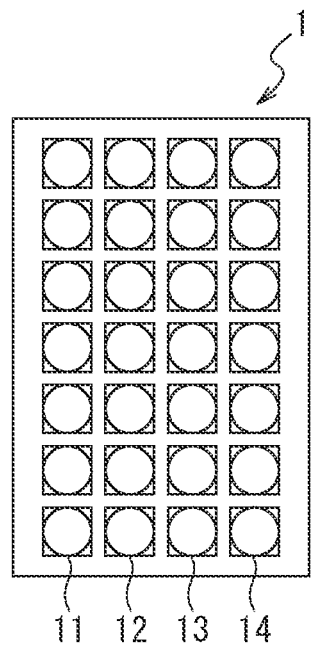
FIG. 17 is a schematic view illustrating a gas sensor included in the lubricant deterioration detection device of the second embodiment.

As the gas sensor 1, a micro gas sensor array produced by MEMS (micro electro mechanical systems) technology can be used, for example. An example of the micro gas sensor array is illustrated in FIG. 17. The micro gas sensor array in FIG. 17 includes seven rows each including four channels 11 to 14. The number of rows can be optional. A larger number of rows can improve detection sensitivity. The first channel 11 selectively detects n-hexanal and n-heptanal. The second channel 12 selectively detects hydrocarbons. The third channel 13 selectively detects water. The fourth channel 14 selectively detects oxygen.

As each sensor included in the micro gas sensor array, a quartz resonator sensor can be used. In the case, for example, a film of polyethylene glycol 2000 is formed on the resonator surface in the first channel 11. In the second channel 12, for example, a polyvinyl chloride (PVC) film is formed on the resonator surface.

In the third channel 13, for example, a poly(3,4-ethylenedioxythiophene)/poly(styrenesulfonate) (PEDOT/PSS: polythiophene-based electrically conductive polymer) film is formed on the resonator surface. In the fourth channel 14, for example, a tin oxide ($SnO_2$) film is formed on the resonator surface. Each film can be formed by spin coating or sputtering, and the film thickness is preferably 50 nm, for example.

As the radio transmitter 2, a radio transmitter including a circuit board 21 can be used, for example. In the case, the circuit board 21 includes a signal processing circuit 211, a transmission circuit 212, an antenna 213, a charging circuit 214, and a secondary battery 215. An input power line 22 of the radio transmitter 2 is connected through the wiring 70 to the thermoelectric conversion element 3. An output power line 23 and an input signal processing line 24 of the radio transmitter 2 are connected through the wiring 60 to the gas sensor 1.

Figure 18:
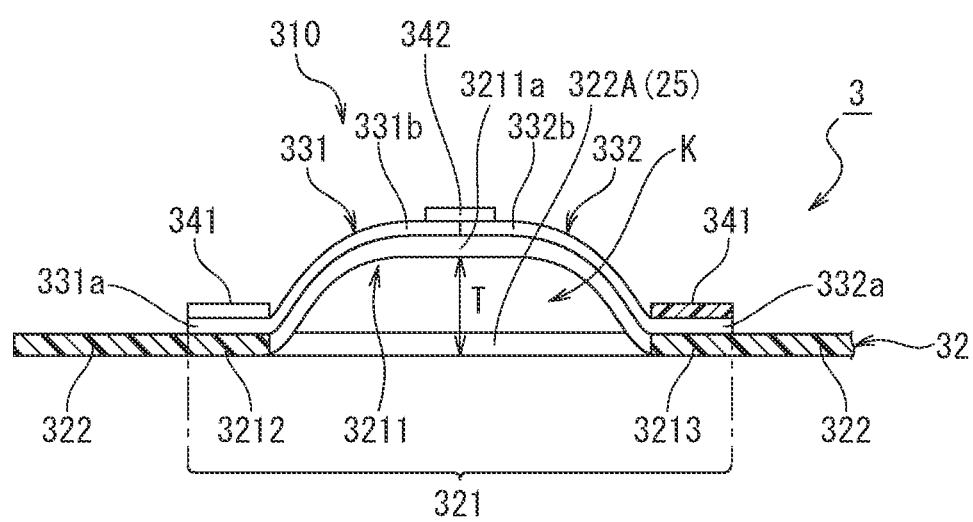
FIG. 18 is a partial cross-sectional view illustrating a thermoelectric conversion element included in the lubricant deterioration detection device of the second embodiment and illustrates a unit formation portion of a substrate corresponding to a single thermoelectric conversion unit and non-formation portions on the respective sides thereof.
Figure 19:
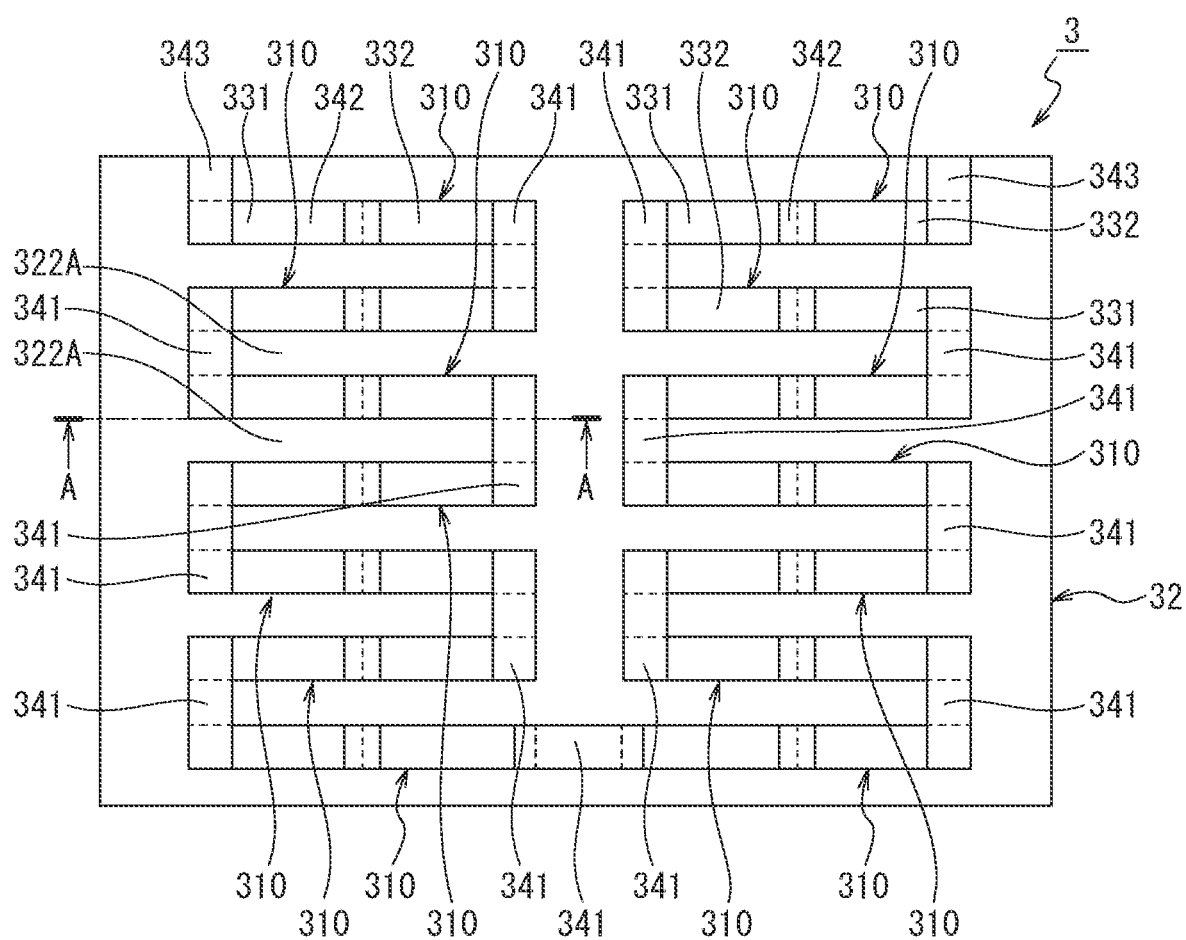
FIG. 19 is a plan view illustrating the state before a projection forming step (after a second print step) of the thermoelectric conversion element included in the lubricant deterioration detection device of the second embodiment.

As the thermoelectric conversion element 3, a thermoelectric conversion element including a flexible substrate 32 and a plurality of thermoelectric conversion units 310 of a printed pattern formed on the substrate 32 can be used, as illustrated in FIG. 18 and FIG. 19. In the case, a cross-sectional shape of a unit formation portion 321 of the substrate 32 on which a thermoelectric conversion unit 310 is formed includes a projection portion 3211, a first base portion part 3212, and a second base portion 3213. The first base portion 3212 and the second base portion 3213 are located at the respective sides of the projection portion 3211, are lower than the projection portion, and are as high as non-formation portions 322 on which no thermoelectric conversion unit 310 is formed.

In the case, as illustrated in FIG. 18, the thermoelectric conversion unit 310 includes a first layer 331 from the first base portion 3212 of the unit formation portion 321 to a top 3211a of the projection portion 3211 and a second layer 332 from the top 3211a to the second base portion 3213. The unit formation portion 321 is separated in the whole region of the projection portion 3211 from a non-formation portion 322A (see FIG. 19) behind the plane of FIG. 18 (appearing below the projection portion 3211). The first layer 331 is formed from a p-type electrically conductive polymer (thermoelectric conversion material), and the second layer 332 is formed from a cured product of silver paste (electrically conductive material).

As the thermoelectric conversion element 3, a thermoelectric conversion element in which 100 of the thermoelectric conversion units 310 illustrated in FIG. 18 are arranged in a 10×10 matrix can be used. In the case, these thermoelectric conversion units 310 are connected in series. FIG. 19 illustrates a thermoelectric conversion element 3 in which 14 thermoelectric conversion units 310 are formed in two columns and seven rows on a substrate 32, for simple explanation. FIG. 18 is a cross-sectional view taken along the line A-A in FIG. 19.

In the case, lower wirings 341 are formed above the first base portions 3212 and the second base portions 3213 through the first layers 331 and the second layers 332 and each connect a first layer 331 and a second layer 332 of the adjacent thermoelectric conversion units 310.

In the case, the first layer 331 and the second layer 332 are formed from different materials, and thus an upper wiring 342 for connecting the first layer 331 and the second layer 332 in each thermoelectric conversion unit 310 is formed at the top 3211a of the projection portion 3211. The ends of the series connection are located on one edge of the substrate 32, and at each position, an external connection terminal 343 is formed.

In the case, each thermoelectric conversion unit 310 has a height difference between a lower part 331a that is a part of the first layer 331 on the first base portion 3212 or a lower part 332a that is a part of the second layer 332 on the second base portion 3213 and upper parts 331b, 332b of the first layer 331 and the second layer 332 on the top 3211a, and the height difference is not less than the thicknesses of the first layer 331 and the second layer 332.

In the case, the substrate 32 of the thermoelectric conversion element 3 is fixed to the cylinder 5, and the pair of connection terminals 343 of the thermoelectric conversion element 3 are connected through the wiring 70 to the power line 22 of the radio transmitter 2.

<Operation of Lubricant Deterioration Detection Device>

When heat generated by rotation of the rolling bearings 4 heats the cylinder 5, a temperature difference is caused between the lower parts 331a, 332a and the upper parts 331b, 332b of each thermoelectric conversion unit 310 included in the thermoelectric conversion element 3. Accordingly, the thermoelectric conversion element 3 generates electricity, and electric current signals produced by the electricity flow through the power line 22 into the charging circuit 214 on the circuit board 21 and are charged in the secondary battery 215.

The electric current in the secondary battery 215 drives the signal processing circuit 211 and the transmission circuit 212 and is supplied through the power line 23 to the gas sensor 1.

Accordingly, the radio transmitter 2 processes detection data input from the gas sensor 1, with the signal processing circuit 211 and the transmission circuit 212 and transmits the result as radio waves from the antenna 213. The display device 20 receives the detection data transmitted as radio waves from the antenna 213 of the radio transmitter 2 and displays the detection result.

<Sensed Result by Sensor Array and Determination Method>

Figure 20:
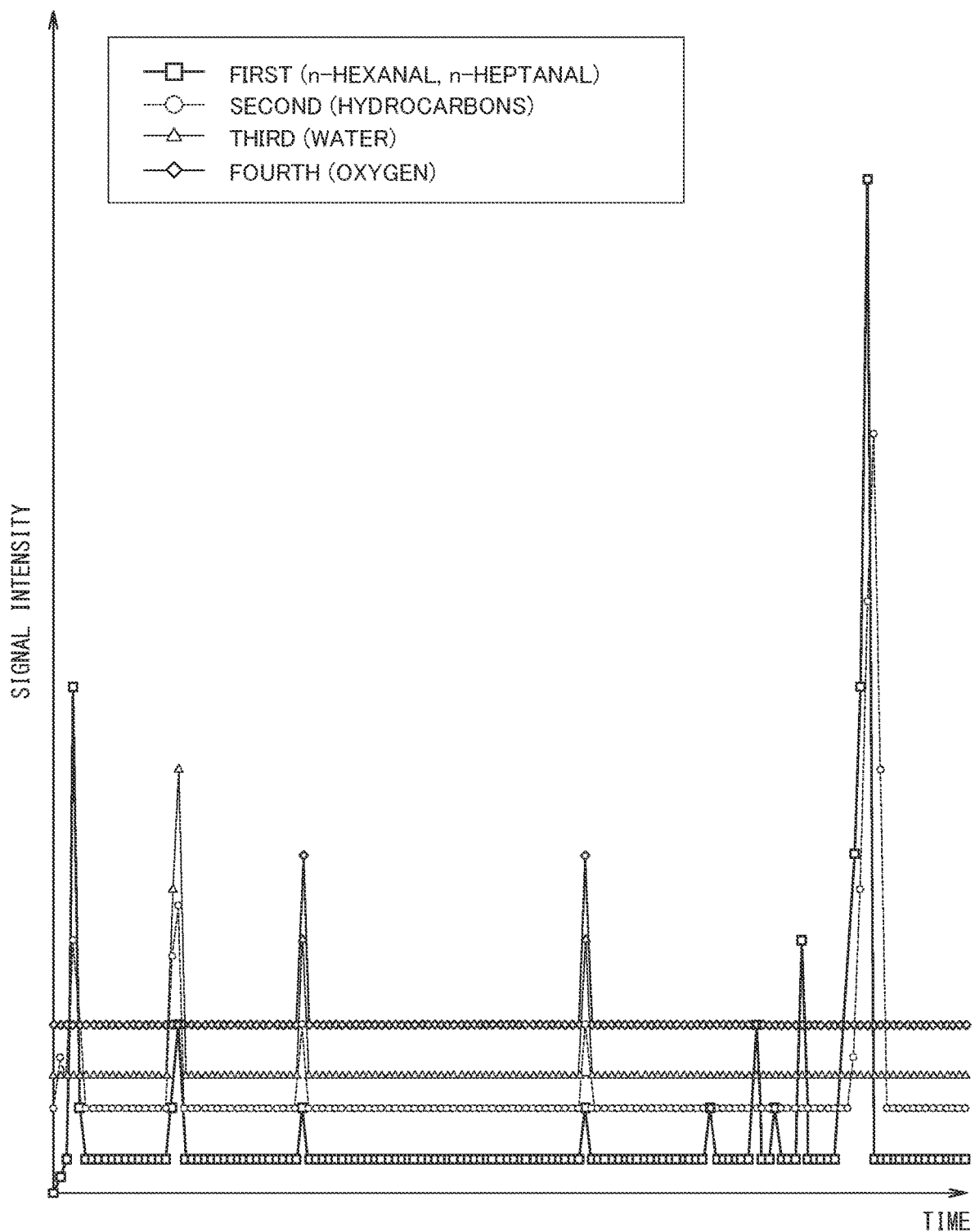
FIG. 20 is a graph illustrative of virtual time courses of component intensities detected by a gas sensor.

A virtual example prepared for explanation of a determination method using the sensor array is illustrated in FIG. 20. The case in which a peak of the first channel (n-hexanal and n-heptanal) 11 and a peak of the second channel (hydrocarbons) 12 are observed at the initial state of rotation will be described. In this case, the peaks are supposed to be formed in the process in which a lubricant is widely spread in and fits with the whole bearing at the initial state of rotation. In other words, at this time point, n-hexanal and/or n-heptanal produced by decomposition of a lubricant that is being spread in the whole bearing and hydrocarbons produced by evaporation of low-molecular weight substances contained in the lubricant in association with a temperature increase are considered to be detected.

The case in which a peak of the first channel 11, a peak of the second channel 12, and a peak of the third channel (water) 13 are subsequently observed will be described. In this case, air (air in the space where the tester is installed) enters a sensor attachment position at this time point, and n-hexanal and/or n-heptanal, hydrocarbons, and water contained in the air are considered to be detected.

The case in which peaks of the first channel 11 and the second channel 12 and peaks of the third channel 13 and the fourth channel (oxygen) 14 are subsequently observed will be described. In this case, exhaust gas from gasoline-fueled cars or the like passing near the tester enters a sensor attachment position at this time point, and oxygen, water, hydrocarbons, and n-hexanal and/or n-heptanal contained in the exhaust gas are considered to be detected.

The case in which only a peak of the first channel 11 is subsequently observed just before seizing up will be described. From the case, detection of only the peak of the first channel 11, or detection of only n-hexanal and/or n-heptanal can be considered to indicate a prediction of seizing up. Hence, if the rotation of a bearing is stopped upon this detection, the breakage of a bearing due to seizing up or damage to other devices can be minimized, and the operation of an apparatus can be safety stopped.

<Effect of Lubricant Deterioration Detection Device>

The lubricant deterioration detection device disclosed in PTL 1 uses a gas sensor that detects at least any gas of hydrocarbons, hydrogen sulfide, and ammonia, whereas the lubricant deterioration detection device in the present embodiment can use a gas sensor 1 that includes a highly sensitive micro gas sensor array prepared by MEMS technology and includes a plurality of channels including a channel for detecting n-hexanal and n-heptanal (first channel 11).

Detection of hydrocarbons indicates evaporation of low-molecular weight substances in association with a temperature increase of a lubricant but does not directly indicate lubricant deterioration.

Hence, the lubricant deterioration detection device of the embodiment should improve the determination accuracy of lubricant deterioration as compared with the lubricant deterioration detection device disclosed in PTL 1.

To attach the lubricant deterioration detection device disclosed in PTL 1 to a rolling bearing, an opening is formed on a circular plate of a shield plate, and a detector including a gas sensor is attached to the opening. The detector and the device main body (display device) are connected through a wiring. In contrast, in the lubricant deterioration detection device of the embodiment, the gas sensor 1, the radio transmitter 2, and the thermoelectric conversion element 3 are fixed onto the outer peripheral surface of the cylinder 5, and the detection result is displayed on the display device 20 wirelessly connected to the gas sensor 1.

In other words, the lubricant deterioration detection device of the embodiment neither damages the rolling bearings 4 nor has any wiring extending from the rolling bearings 4 to the display device 20. Lubricant deterioration can be continuously monitored on the display device 20 located apart from the rolling bearings 4.

<Sensor Selectively Detecting n-Hexanal, n-Heptanal>

Examples of the material of the film selectively adsorbing at least one of n-hexanal and n-heptanal include polynaphthylamine, high-density polyethylene, EVOH (ethylene-vinyl alcohol copolymer), dinitrophenylhydrazine, nitroterephthalic acid-modified polyethylene glycol, polyethyleneimine, and ABS resins, in addition to polyethylene glycol.

When a polynaphthylamine film is compared with a polyethylene glycol film as the film formed on the resonator surface of a quartz resonator sensor, the quartz resonator sensor using the polyethylene glycol film achieves higher sensitivity of detecting n-hexanal and n-heptanal than that using the polynaphthylamine film. Hence, the polyethylene glycol film is preferably used.

<Method for Producing Thermoelectric Conversion Element>

A method for producing the thermoelectric conversion element 3 will be described with a thermoelectric conversion element including 14 thermoelectric conversion units 310 in two columns and seven rows.

Figure 21:
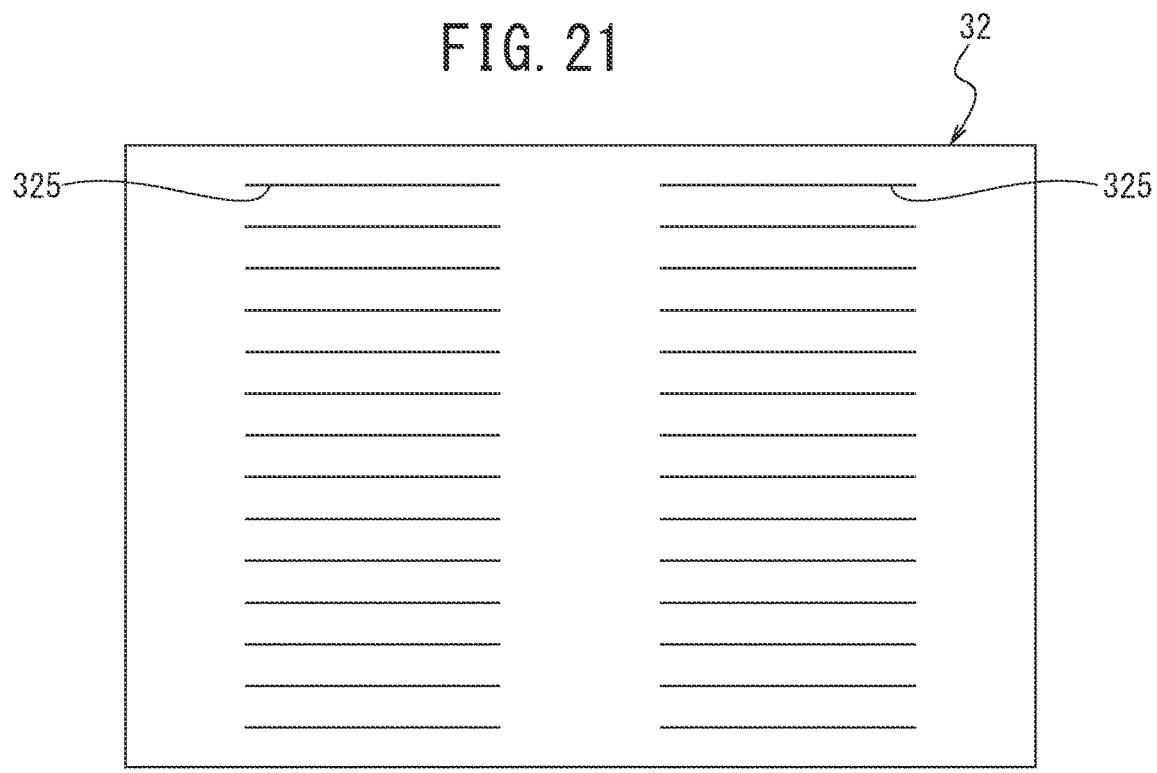
FIG. 21 is a plan view illustrative of a slit forming step included in a method for producing the thermoelectric conversion element illustrated in FIG. 18.
Figure 22:
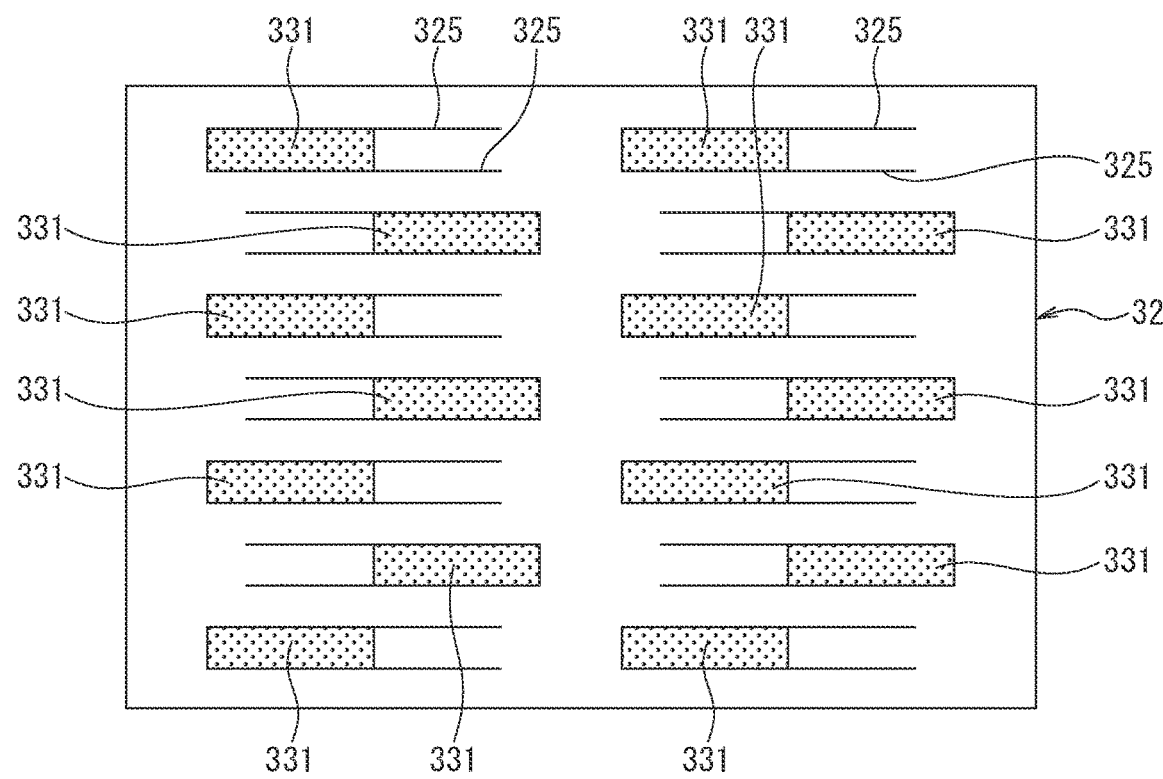
FIG. 22 is a plan view illustrative of a former step in a first print step included in the method for producing the thermoelectric conversion element illustrated in FIG. 18.
Figure 23:
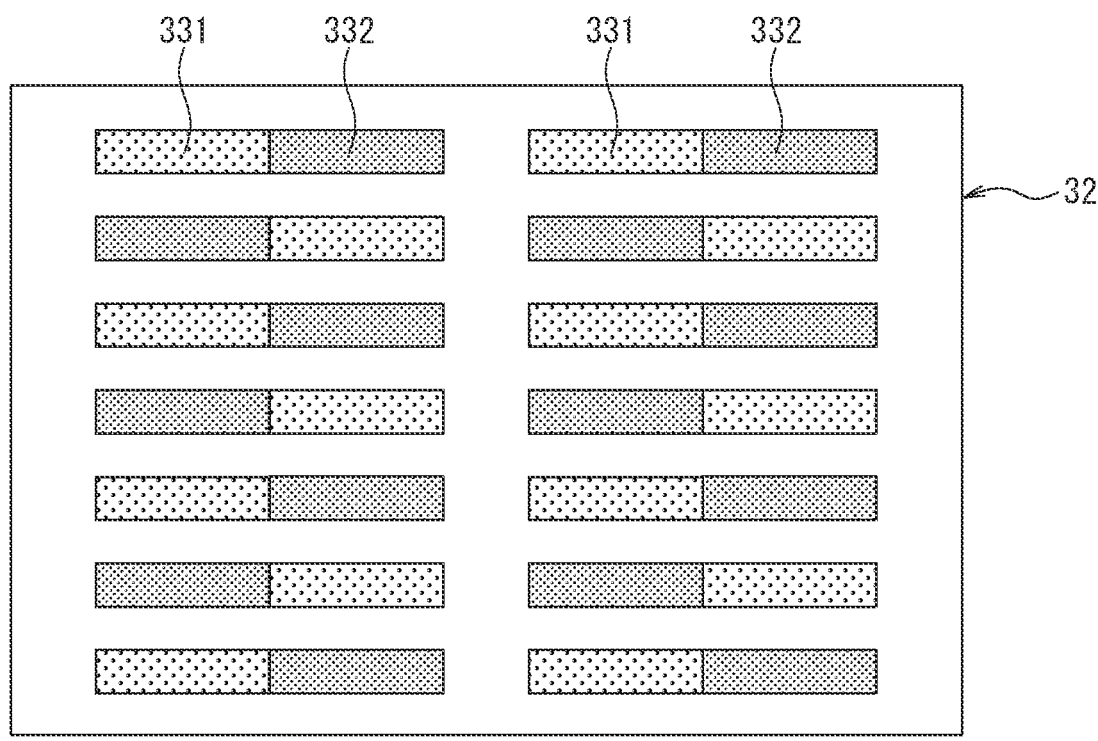
FIG. 23 is a plan view illustrative of a latter step in the first print step included in the method for producing the thermoelectric conversion element illustrated in FIG. 18.
Figure 24:
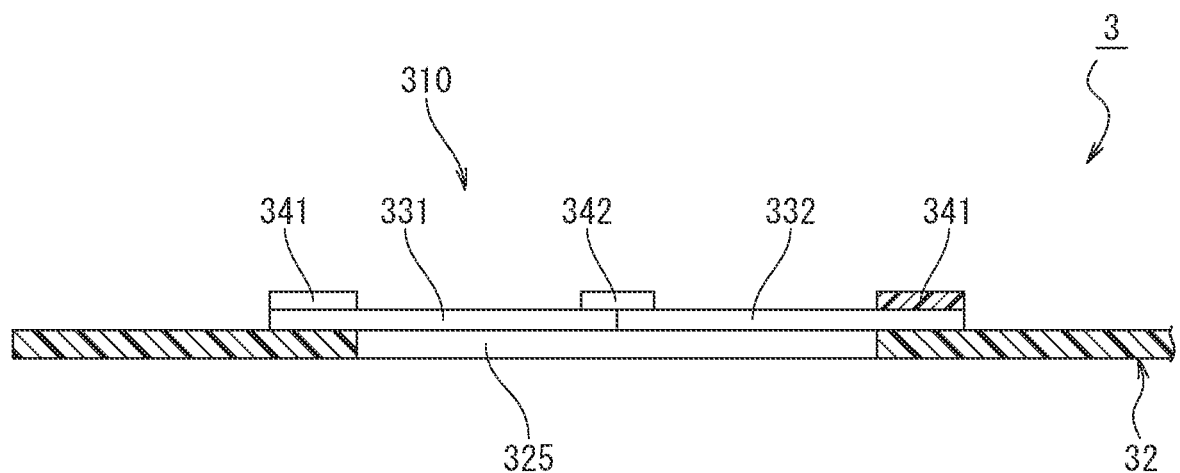
FIG. 24 is a cross-sectional view taken along the line A-A in FIG. 19.

The thermoelectric conversion element 3 is produced by performing a slit forming step illustrated in FIG. 21, a former step in a first print step illustrated in FIG. 22, a latter step in the first print step illustrated in FIG. 23, a second print step illustrated in FIG. 19, and a projection forming step of making the state in FIG. 24 into the state in FIG. 18, in this order.

In the method for producing the thermoelectric conversion element 3 in the embodiment, 28 slits 325 corresponding to 14 thermoelectric conversion units 310 illustrated in FIG. 19 are first formed on a substrate 32, as illustrated in FIG. 21. The slits 325 are formed to have the same length as the formation distance of a pair of lower wirings 341 in a thermoelectric conversion unit 310. In other words, slits 325 are formed in the entire region of the substrate 32 in which projection portions 3211 are formed.

Next, as the former step in the first print step, a first layer 331 is formed for each thermoelectric conversion unit 310 in the width between two adjacent slits 325 in each column, as illustrated in FIG. 22. Adjacent first layers 331 in a column or between columns of 14 thermoelectric conversion units 310 in the two columns are provided at opposite positions in the length direction of the slits 325. An end of each first layer 331 along the slits 325 protrudes outward from the slits 325.

Next, as the latter step in the first print step, a second layer 332 is formed for each thermoelectric conversion unit 310 in the width between two adjacent slits 325 in each column, as illustrated in FIG. 23. The second layer 332 is formed in contact with the adjacent first layer 331 to have the same thickness as that of the first layer 331.

Through the process, a thermoelectric conversion pattern including all the first layers 331 and the second layers 332 constituting 14 thermoelectric conversion units 310 in two columns are formed on the substrate 32. In the state of FIG. 23, the portions including the first layers 331 and the second layers 332 on the substrate 32 are unit formation portions, and the other portions are non-formation portions.

Next, as the second print step, a conductive layer pattern including lower wirings 341, connection terminals 343, and upper wirings 342 is formed as illustrated in FIG. 19, on the thermoelectric conversion pattern illustrated in FIG. 23. The thermoelectric conversion units 310 in the state are formed in a planar shape on the planar substrate 32, as illustrated in FIG. 24.

Next, as the projection forming step, a mold having male portions corresponding to the projection portion 3211 in FIG. 18 is pressed against the back face of the substrate 32 where the slits 325 are formed (face without the thermoelectric conversion units 310). This pressing draws and deforms the first layers 331, the second layers 332, and portions of the substrate 32 with the first layers 331 and the second layers 332, forming projection portions 3211. For the pressing, a mold having male portions corresponding to the projection portions 3211 of all the unit formation portions 321 is used to form the projection portions 3211 for all the thermoelectric conversion units 310 at once.

In the thermoelectric conversion element 3 produced in this manner, each thermoelectric conversion unit 310 has a height difference between the lower part 331a that is a part of the first layer 331 on the first base portion 3212 or the lower part 332a that is a part of the second layer 332 on the second base portion 3213 and the upper parts 331b, 332b of the first layer 331 and the second layer 332 on the top 3211a, and the height difference is not less than the thicknesses of the first layer 331 and the second layer 332.

Hence, even when the thermoelectric conversion element 3 is placed on a planar heating element (for example, a hot plate) while the non-formation portion 322 of the substrate 32 is horizontally held and the lower parts 331a of the first layers 331 and the lower parts 332a of the second layers 332 are heated through the substrate 32, high electric power generation performance can be achieved. In addition, the substrate 32 with the printed pattern can be simply, stably installed on a heating element.

The whole region of the projection portion 3211 in each unit formation portion 321 is separated from non-formation portions 322A. Lower spaces K of the projection portions 3211 thus continue to form an air flow path in each column of the thermoelectric conversion units 310. Hence, by flowing air through the flow paths including the lower spaces K to cool the tops 3211a at the time of heating of the substrate 32, a larger temperature difference can be produced between the lower parts 331a, 332a and the upper parts 331b, 332b of the thermoelectric conversion units 310.

Preferred Embodiment

The lubricant deterioration detection device in the second aspect of the present invention includes a gas sensor configured to detect at least one of n-hexanal and n-heptanal. The gas sensor preferably has a plurality of channels including a channel that selectively detects at least one of n-hexanal and n-heptanal.

An example of the lubricant deterioration detection device in the second aspect of the invention is a lubricant deterioration detection device further including a radio transmitter that wirelessly transmits a detection result by the gas sensor to a receiver and a stand-alone power supply that includes a thermoelectric conversion element and supplies electric power to the gas sensor and the radio transmitter.

The thermoelectric conversion element included in the stand-alone power supply preferably has the following structures (a) to (d) or (a) to (e).

(a) A substrate and a plurality of thermoelectric conversion units formed on the substrate are included.

(b) A cross-sectional shape of a unit formation portion with each thermoelectric conversion unit on the substrate includes a projection portion, a first base portion, and a second base portion, the first base portion and the second base portion are located at the respective sides of the projection portion and are lower than the projection portion, and a non-formation portion without the thermoelectric conversion unit on the substrate is at a lower position than the top of the projection.

(c) The thermoelectric conversion unit includes a first layer from the first base portion of the unit formation portion to the top of the projection portion and a second layer from the top to the second base portion. At least one of the first layer and the second layer is formed from a thermoelectric conversion material. The first layer and the second layer are formed from the same material or different materials. The plurality of thermoelectric conversion units are connected in series.

(d) Lower wirings are formed above the first base portion and the second base portion and each connect the first layer and the second layer of the adjacent thermoelectric conversion units. When the first layers and the second layers are formed from different materials, an upper wiring connecting the first layer and the second layer in each thermoelectric conversion unit is formed at the top. External connection terminals are provided at the respective ends of the series connection.

(e) Each unit formation portion is separated in the region of the projection from the non-formation portion.

Third Aspect

[Discussion by Inventors]

With the method of evaluating the deterioration state of a lubricant in a rolling bearing by the amount of hydrocarbons contained in a gas in the rolling bearing, different amounts of hydrocarbons may be detected even when the deterioration state of a lubricant is the same because different operation conditions of a rolling bearing (rotation speed or changes in load) may result in various temperature increases of the lubricant. Hence, the threshold of the hydrocarbon detection amount indicating deterioration is required to be changed depending on operation conditions of a rolling bearing. The threshold change is a complicated operation, and deviation of the threshold from an appropriate value may cause misjudgment of lubricant deterioration.

The inventors of the present application have studied to solve the problem and have revealed that the amount of carbonyl compounds (aldehydes and ketones) contained in the gas in a rolling bearing is substantially 0 before lubricant deterioration regardless of operation conditions of the rolling bearing, gradually increases just before seizing up by the lubricant, and then increases sharply.

On the basis of the findings, it has been thought that a lubricant deterioration detection device including a gas sensor that selectively detects carbonyl compounds can determine the deterioration state of a lubricant in a rolling bearing with higher accuracy than a lubricant deterioration detection device including a gas sensor that detects hydrocarbons, and the invention is achieved.

Third Embodiment

An embodiment in a third aspect of the present invention will now be described, but the invention is not limited to the following embodiment. The following embodiment includes technically preferred limitations for carrying out the invention, but the limitations are not essential requirements of the invention.

Figure 25:
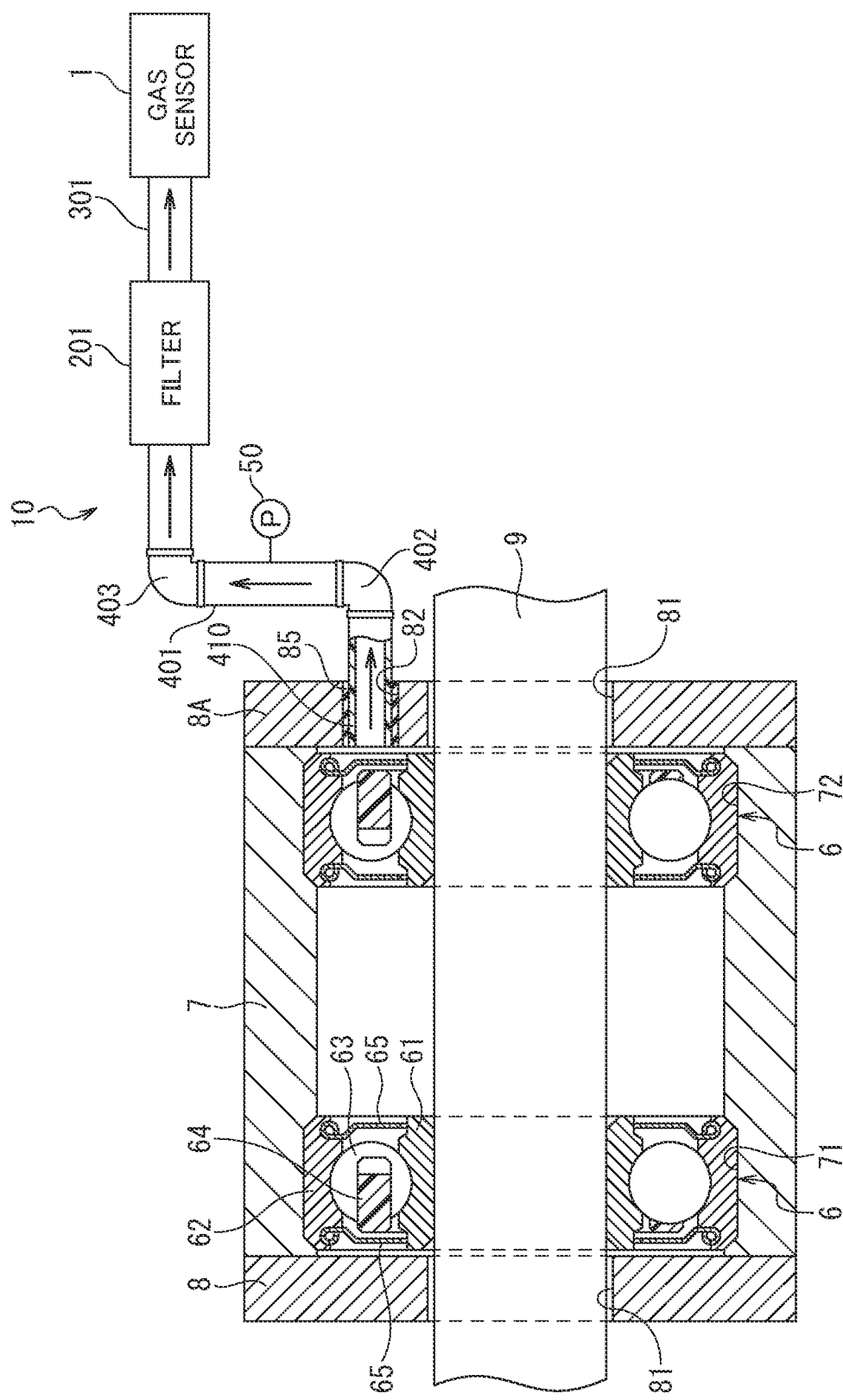
FIG. 25 is a view illustrating a lubricant deterioration detection device of a third embodiment attached to a member that closes an axial end of a cylinder portion to which outer rings of rolling bearings are fixed.
Figure 26:
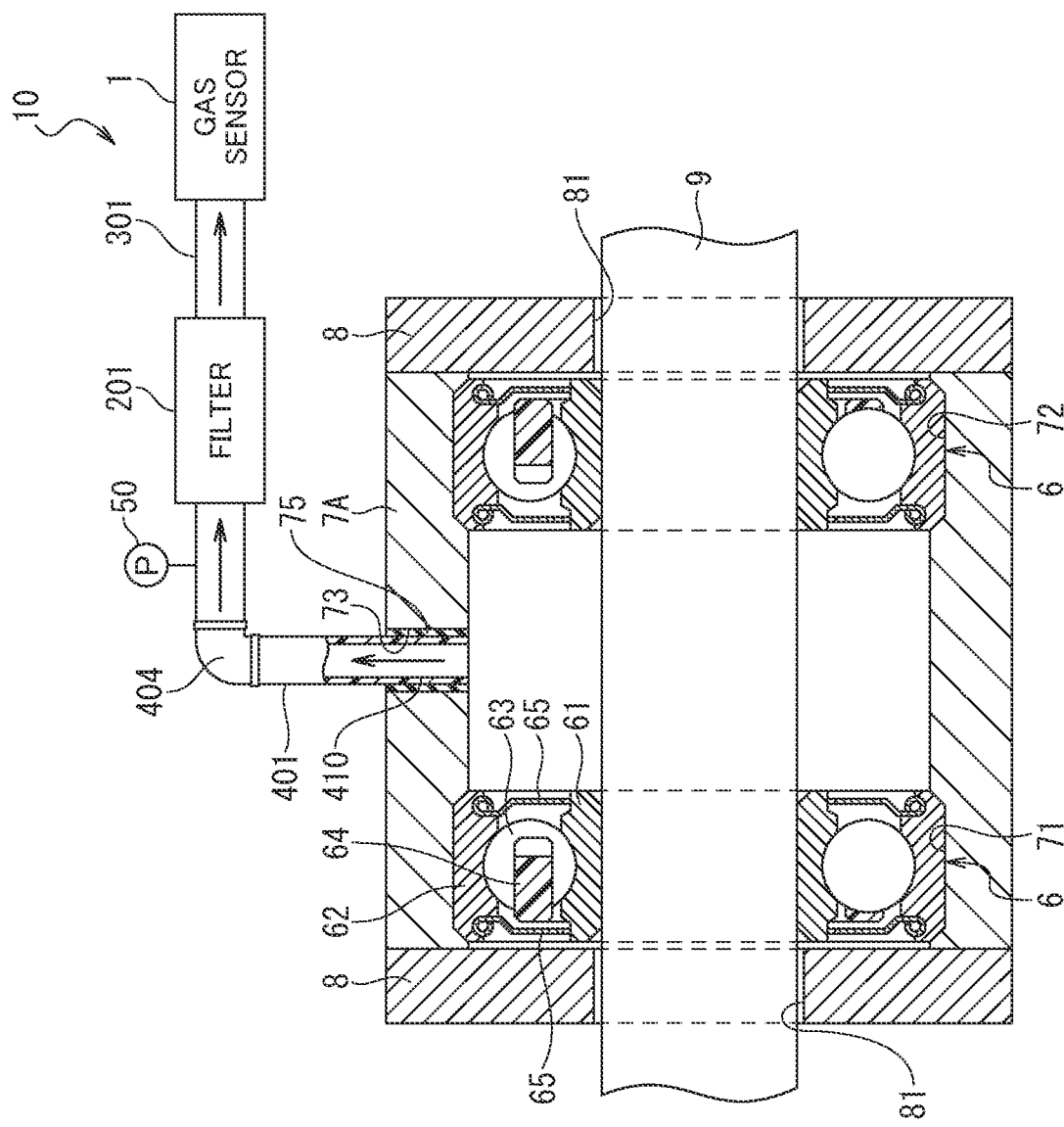
FIG. 26 is a view illustrating a lubricant deterioration detection device of the third embodiment attached to the axial center of a cylinder portion to which outer rings of rolling bearings are fixed.

As illustrated in FIG. 25 and FIG. 26, the lubricant deterioration detection device 10 of the embodiment includes a gas sensor 1, a filter 201, gas inlet pipes 301, 401, and a suction pump 50. The gas inlet pipe 301 connects a gas inlet port of the gas sensor 1 and a gas outlet port of the filter 201. One end of the gas inlet pipe 401 is a gas inlet portion 410 of the lubricant deterioration detection device, and the other end is connected to a gas inlet port of the filter 201.

In the example in FIG. 25, the gas inlet pipe 401 includes three straight pipes and two elbow pipes, extends through an elbow pipe 402 in the direction perpendicular to the extending direction of the gas inlet portion 410, and extends through an elbow pipe 403 in the same direction as the extending direction of the gas inlet portion 410. The suction pump 50 is connected to a point between the elbow pipes 402, 403 of the gas inlet pipe 401. In the example in FIG. 26, the gas inlet pipe 401 includes two straight pipes and an elbow pipe and extends through an elbow pipe 404 to a direction perpendicular to the extending direction of the gas inlet portion 410. The suction pump 50 is connected to a point between the elbow pipe 404 of the gas inlet pipe 401 and the filter 201.

The gas sensor 1 is a controlled potential electrolysis sensor that detects only aldehydes (carbonyl compounds). The gas sensor 1 includes a display device that displays a real time aldehyde concentration. As the filter 201, a ceramic filter that removes oil mist is provided.

The device to which the lubricant deterioration detection device 10 is attached includes two identical rolling bearings 6, a cylinder portion 7, and circular plate portions 8, 8A each having a central hole 81 in the example in FIG. 25. In the example in FIG. 26, the device includes two identical rolling bearings 6, a cylinder portion 7, and two identical circular plate portions 8 each having a central hole 81. The cylinder portion 7 is a bearing housing in which outer rings of the rolling bearings are fitted.

In the example in FIG. 25, the cylinder portion 7 and the circular plate portions 8, 8A constitute a housing that rotatably stores two rolling bearings 6. In the example in FIG. 26, the cylinder portion 7 and the two identical circular plate portions 8 constitute a housing that rotatably stores two rolling bearings 6.

Each of the two rolling bearings 6 is a sealed deep groove ball bearing including an inner ring 61, an outer ring 62, balls (rolling elements) 63, a retainer 64, and shield plates (noncontact seals) 65 and is lubricated with a lubricant. At the respective axial ends of the cylinder portion 7 on the inner peripheral surface, grooves 71, 72 are formed for fitting the outer rings 62 of the two rolling bearings 6.

The circular plate portion 8A used in the example in FIG. 25 has a through hole 82 penetrating in the axis direction at a position facing a shield plate 65. The cylinder portion 7A used in the example in FIG. 26 has a through hole 73 penetrating in a direction orthogonal to the axis, at the axial center.

The two rolling bearings 6 are fixed to the cylinder portion 7 apart from each other in the axis direction by fitting the outer rings 62 to the corresponding grooves 71, 72. The respective axial ends of the cylinder portion 7 are closed by the circular plate portions 8, 8A in the example in FIG. 25 or by the two circular plate portions 8 in the example in FIG. 26. A rotating shaft 9 fitted to the inner rings 61 of the two rolling bearings 6 penetrates the central holes 81, extends outward from the circular plate portions 8, 8A in the example in FIG. 25 or extends outward from the two circular plate portions 8 in the example in FIG. 26, and is connected to a rotation device not shown in the drawings.

In the example in FIG. 25, the gas inlet portion 410 of the lubricant deterioration detection device 10 is inserted through a cylindrical-shaped rubber member 85 into the through hole 82 of the circular plate portion 8A, and the gap between the gas inlet portion 410 and the through hole 82 is sealed by the rubber member 85. In the example in FIG. 26, the gas inlet portion 410 of the lubricant deterioration detection device 10 is inserted through a cylindrical-shaped rubber member 75 into the through hole 73 of the cylinder portion 7A, and the gap between the gas inlet portion 410 and the through hole 73 is sealed by the rubber member 75.

The lubricant deterioration detection device 10 functions as follows: By activating the suction pump 50 concurrently with the rotation start of the rolling bearings 6, the gas in the space surrounded by the rolling bearings 6, the cylinder portion 7, and the circular plate portions 8 (8A) is sucked.

The sucked gas passes through the gas inlet pipe 401 into the filter 201, and the filter 201 removes oil mist. Subsequently, the gas passes through the gas inlet pipe 301 into the gas sensor 1, then the gas sensor 1 determines the aldehyde concentration, and the result is displayed.

The aldehyde concentration of a gas sucked into the gas inlet pipe 401 of the lubricant deterioration detection device 10 is substantially 0 before deterioration of a lubricant in the rolling bearings 6, gradually increases just before seizing up by the lubricant, and then increases sharply. Hence, the deterioration of a lubricant in the rolling bearings 6 can be identified when the gas sensor 1 starts to detect increasing aldehyde concentrations.

If a lubricant or components other than the components generated from a lubricant adhere to the gas sensor 1, the gas sensor 1 may malfunction, or the detection accuracy of the gas sensor 1 may deteriorate. To address this, the lubricant deterioration detection device 10 in the embodiment includes a filter 201 between the gas sensor 1 and the gas inlet portion 410. As the filter 201, an oil mist-removing filter is provided. In place of the oil mist-removing filter, a wet dust collector or a static oil mist remover may be provided.

Examples of the oil mist-removing filter include a paper filter, a metal filter, a ceramic filter, and a CNP filter. Of these filters, a paper filter is preferably used in terms of easy exchange. As the paper filter, a paper filter having a mesh size of about 200 and capable of collecting oil mist particles having a particle size of 0.3 μm or more is preferably used.

Between the gas sensor 1 and the gas inlet portion 410, a filter that removes smelling components other than aldehydes may be provided. Examples of the filter that removes smelling components other than aldehydes (for example, smelling components generated from industrial wastes of factories) include a photocatalytic filter and an activated carbon filter. Specifically preferred is a filter in which an adsorbent and a photocatalytic powder are packed in the space (cavities) between a nonwoven fabric and a film. The adsorbent is preferably activated carbon and silica gel, and the photocatalyst is preferably titanium oxide and zinc oxide.

Alternatively, the difference between a gas having passed through a filter that adsorbs aldehydes, such as a dinitrophenylhydrazine (DNPH) filter, and a gas not having passed can be analyzed to determine aldehydes.

<Verification Test of Lubricant Deterioration Detection by Lubricant Deterioration Detection Device 10: Test 1>

The device illustrated in FIG. 27 was used to perform the verification test for examining the lubricant deterioration detection result by the lubricant deterioration detection device 10. The device illustrated in FIG. 27 is prepared as follows: the elbow pipe 402 that connects a portion of the gas inlet pipe 401 with the suction pump 50 to the gas inlet portion 410 in the example in FIG. 25 is replaced with a branch pipe 405, and the opposite side of the branch pipe 405 to the gas inlet pipe 401 is connected to one end of a gas inlet pipe 104 included in a lubricant deterioration detection device 100 of a comparative example. As the electrode included in the controlled potential electrolysis sensor of the gas sensor 1, a platinum electrode was used.

The lubricant deterioration detection device 100 includes a smell sensor 101, a filter 102, gas inlet pipes 103, 104, and a suction pump 105. The gas inlet pipe 103 connects a gas inlet port of the smell sensor 101 and a gas outlet port of the filter 102. The other end of the gas inlet pipe 104 is connected to a gas inlet port of the filter 102. The suction pump 105 is connected to a portion of the gas inlet pipe 104 connected to the branch pipe 405. The smell sensor 101 is an indium oxide-based heat ray sintered semiconductor sensor and can determine odor index. As the filter 102, the same oil mist-removing filter as the filter 201 was used.

As two rolling bearings 6, rolling bearings each having an inner diameter of 25 mm, an outer diameter of 62 mm, and a width of 17 mm were prepared. Each rolling bearing 6 was lubricated with a grease. The grease used was a commercially available grease containing a lithium soap (consistency: No. 2) as a thickener and a mineral oil (dynamic viscosity at 40° C.: 100 mm$^2$/s) as a base oil.

The outer ring 62 of each rolling bearing 6 was fitted to the corresponding groove 71, 72 on the cylinder portion 7, a rotating shaft 9 of a tester is fitted to the inside of the inner ring 61 of each rolling bearing 6, and the gas inlet portion 410 of the lubricant deterioration detection devices 10, 100 was attached to the circular plate portion 8A, giving the state illustrated in FIG. 27. The through hole 82 in the circular plate portion 8A has a diameter of 6.5 mm, and the gas inlet pipe 401 has an outer diameter of 6 mm and an inner diameter of 4 mm. The gap between the through hole 82 and the gas inlet pipe 401 is sealed by a rubber member 85.

While a radial load of 98 N and an axial load of 1,470 N were applied to each rolling bearing 6, the rotating shaft 9 was continuously rotated at a rotation speed of 10,000 min$^{-1}$. Concurrently with the rotation start of the rotating shaft 9, the lubricant deterioration detection devices 10, 100 were driven, and the aldehyde concentration detection by the gas sensor 1, the odor index measurement by the smell sensor 101, and the outer ring temperature measurement were continuously performed. The results are illustrated as the graphs in FIGS. 28A to 28C. The rotation of the rotating shaft 9 and the driving of the lubricant deterioration detection devices 10, 100 were so controlled as to be stopped when an abnormal increase of the outer ring temperature was detected.

At 208 hours after the test start, an abnormal increase of the outer ring temperature was detected, and the rotation of the rotating shaft 9 and the driving of the lubricant deterioration detection devices 10, 100 were stopped.

Figure 28A:
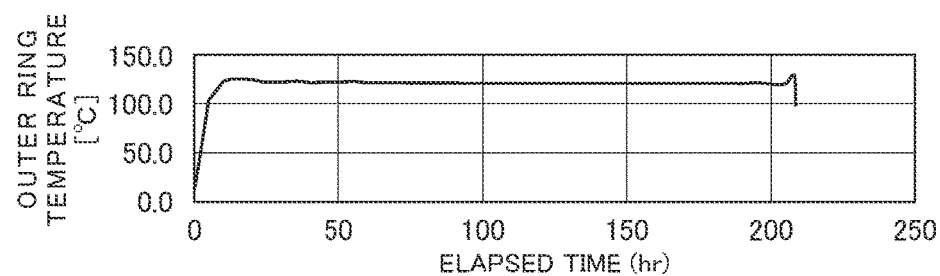
FIGS. 28A to 28C are graphs obtained in test 1 performed in the third embodiment.
Figure 28B:
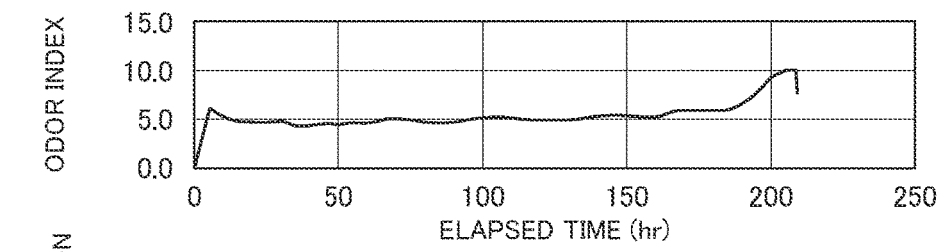
Figure 28C:
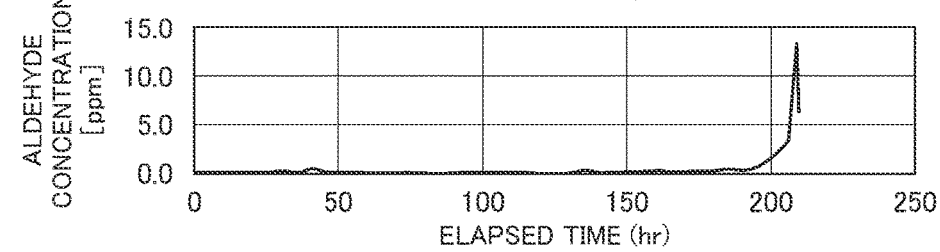

The graphs in FIGS. 28A to 28C reveal the following findings.

FIG. 28A is a graph illustrating the relation between elapsed time and outer ring temperature. The outer ring temperature increased after the test start, then was almost constant from about 10 hours, and exceeded 125° C. at 208 hours.

FIG. 28B is a graph illustrating the relation between elapsed time and odor index detected by the smell sensor 101. The odor index increased at substantially the same rate as the increase rate of the outer ring temperature and then was almost constant at around 5.0 when the outer ring temperature became almost constant. Subsequently, the odor index slightly increased at around 165 hours, then was constant at about 6.0, and started to increase from 185 hours.

FIG. 28C is a graph illustrating the relation between elapsed time and aldehyde concentration determined by the gas sensor 1. The aldehyde concentration was almost 0 immediately after the test start until 180 hours, then gradually increased from 180 hours, and sharply increased from 206 hours that was immediately before the detection of the abnormal increase of the outer ring temperature.

The test results reveal the following findings.

The lubricant deterioration detection devices 10, 100 can identify lubricant deterioration in advance.

With the lubricant deterioration detection device 10 of the embodiment, the aldehyde concentration was substantially 0 immediately after the test start until lubricant deterioration was caused in the rolling bearings 6, gradually increased just before seizing up by the lubricant, and then increased sharply. Hence, the deterioration of a lubricant in the rolling bearings 6 can be identified when the gas sensor 1 starts to detect increasing aldehyde concentrations.

With the lubricant deterioration detection device 100 of the comparative example, the odor index increased immediately after the test start, then was almost constant before lubricant deterioration was caused in the rolling bearings 6, and gradually increased just before seizing up by the lubricant. Hence, by setting the threshold of the odor index at, for example, 7.0, lubricant deterioration in the rolling bearings 6 can be identified when the odor index reaches the threshold. In other words, the lubricant deterioration detection device 100 of the comparative example needs previous threshold setting depending on conditions of use. In addition, the odor index varies with conditions of use of a rolling bearing, and thus an apparatus including a plurality of rolling bearings needs threshold setting for the respective bearings, which is a complicated process.

As described above, the lubricant deterioration detection device 100 of the comparative example needs previous threshold setting, and thus a setting error of the threshold may lead to incorrect determination of lubricant deterioration. In contrast, the lubricant deterioration detection device 10 of the embodiment eliminates the necessity of threshold setting depending on conditions of use. An example of the threshold is 1.0 ppm from the graph in FIG. 28C. Hence, the lubricant deterioration detection device 10 of the embodiment can determine the deterioration state of a lubricant with higher accuracy than the lubricant deterioration detection device 100 of the comparative example.

<Test 2>

A test of determining aldehyde concentrations in a closed space was performed by heating a closed space containing a grease to increase the grease temperature. The grease used was the same as that used in the test 1. The aldehyde concentration was determined by using the gas sensor 1 and the filter 201 used in the test 1.

Figure 29:
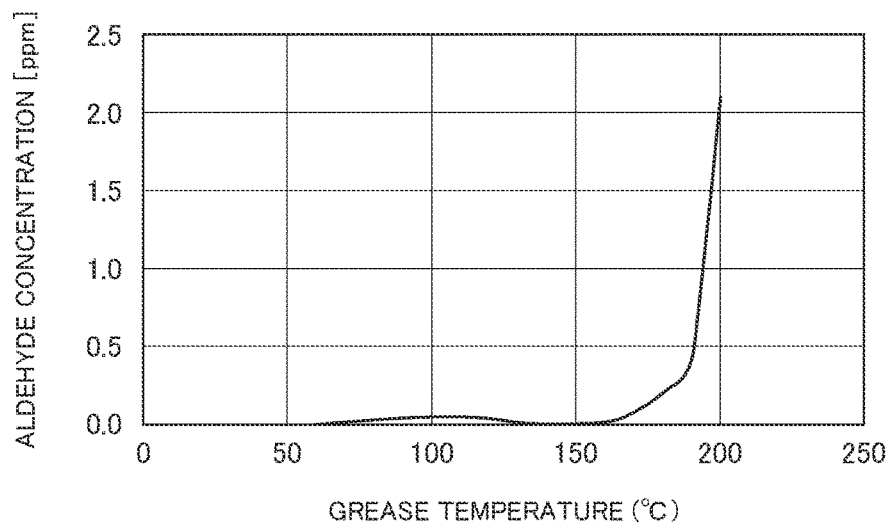
FIG. 29 is a graph illustrating the relation between temperature and aldehyde concentration in a closed space, obtained in test 2 performed in the third embodiment.

Specifically, 20 mg of grease was thinly applied onto an aluminum foil, and the aluminum foil was placed in a closed space having a volume of 25 mL. A pipe was attached to a side wall defining the closed space, and a gas through the filter 201 was analyzed by the gas sensor 1. As a result, an aldehyde was started to be clearly detected when the temperature in the closed space exceeded about 160° C., and the aldehyde concentration sharply increased when the temperature exceeded 190° C. and reached 200° C., as illustrated in FIG. 29.

The test 1 has revealed that the outer ring temperature when the aldehyde concentration sharply increased was 120° C. to 130° C., and the results of the test 1 and the test 2 reveal that the temperature of the grease in the bearing is higher than the temperature of the outer ring when the aldehyde concentration sharply increases.

<Verification of Initial Stage in Test 1>

Figure 30A:
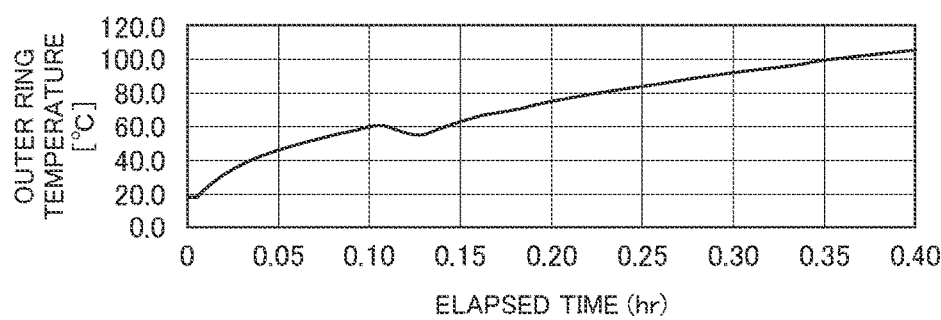
FIGS. 30A to 30C are graphs obtained in test 1 performed in the third embodiment and are enlarged graphs of those in FIGS. 28A to 28C before 0.4 hours as the elapsed time.
Figure 30B:
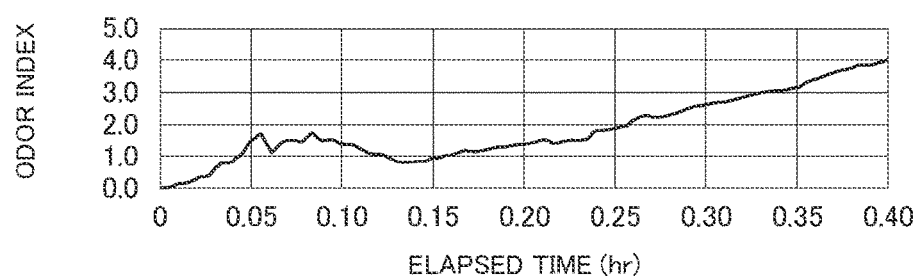
Figure 30C:
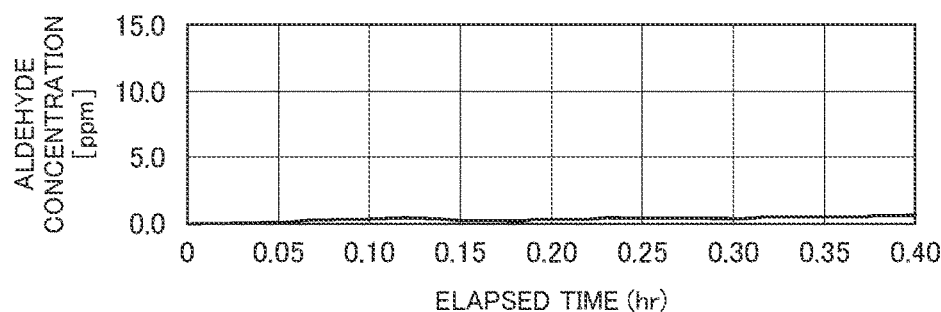

FIGS. 30A to 30C indicate that, in the initial stage of test 1, the odor detection amount increased almost in proportion to the outer ring temperature, whereas almost no aldehyde was detected. The result of the test 2 indicates that an aldehyde concentration was detected when the grease reached a certain temperature or higher.

These results indicate that detection of both the odor amount and the aldehyde concentration enables simple evaluation of the temperature in a bearing. It is difficult to directly measure the temperature in a bearing, and thus this evaluation method is useful. The reason of the difficult measurement includes rolling elements rolling on an orbital plane through a grease and difficulty in making a hole in a bearing member.

<Monitoring of Lubricant Deterioration>

The lubricant deterioration detection device 10 in FIG. 26 was used to continuously monitor the deterioration state of a lubricant in a rolling bearing.

As two rolling bearings 6, rolling bearings each having an inner diameter of 70 mm, an outer diameter of 110 mm, and a width of 20 mm and including steel balls 63 were prepared. Each rolling bearing 6 was lubricated with a grease. The grease used was a commercially available grease containing a barium complex soap (consistency: No. 2) as a thickener and a mixed oil of mineral oil and ester oil (dynamic viscosity at 40° C.: 23 mm$^2$/s) as a base oil.

While an axial load of 200 N was applied to each rolling bearing 6, a rotating shaft 9 was rotated at a rotation speed of 14,000 min$^{-1}$ for 20 hours and then was rotated at a rotation speed of 2,000 min$^{-1}$ for 4 hours. This cycle was repeated to continuously rotate the rotating shaft 9. Concurrently with the rotation start of the rotating shaft 9, the lubricant deterioration detection device 10 was driven, and the aldehyde concentration detection by the gas sensor 1 and the outer ring temperature measurement were continuously performed.

As a result, an abnormal increase of the outer ring temperature was detected at 303 hours after the test start. At this point, the detected aldehyde concentration was about 20 times as high as the normal concentration. At 500 hours after the test start, the lubricant deterioration detection device 10 was manually stopped. In the rolling bearing 6 after the test, damages and discoloration probably resulting from seizing up were observed on the orbital plane.

Alternative Embodiment

Figure 31:
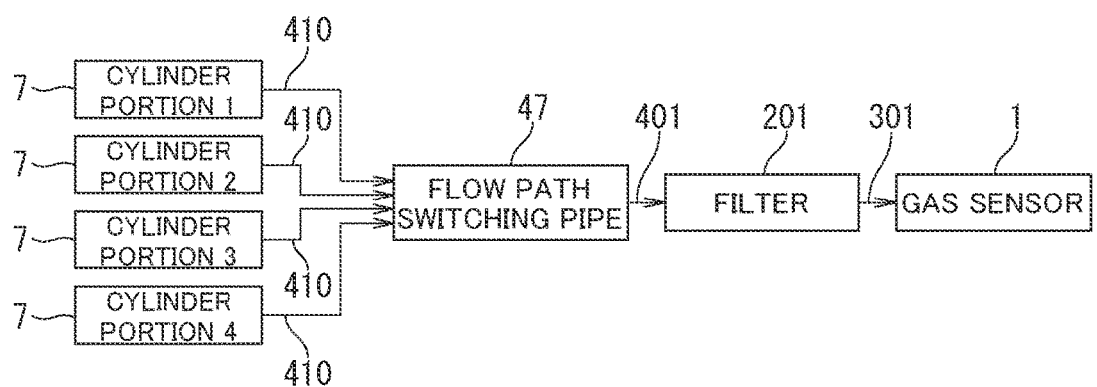
FIG. 31 is a view illustrating a single lubricant deterioration detection device capable of evaluating lubricant deterioration of a plurality of rolling bearings.

A lubricant deterioration detection device of an alternative embodiment illustrated in FIG. 31 is prepared as follows: the elbow pipe 402 that connects a portion of the gas inlet pipe 401 with the suction pump 50 to the gas inlet portion 410 in the lubricant deterioration detection device 10 in FIG. 25 is replaced with a flow path switching pipe 47, and the flow path switching pipe 47 is connected to a plurality of gas inlet portions 410. Each of the plurality of gas inlet portions 410 is inserted into a through hole 73 (82) formed in a corresponding cylinder portion 7 (or a circular plate portion 8A) through a rubber member 75 (85), and the gap between the gas inlet portion 410 and the through hole 73 (82) is sealed.

In the example illustrated in FIG. 31, by switching the flow path switching pipe 47, the aldehyde concentrations contained in gases in the plurality of cylinder portions (bearing housings) 7 can be determined by a single gas sensor 1. In other words, lubricant deterioration of rolling bearings fixed in a plurality of cylinder portions (bearing housings) 7 can be evaluated by a single lubricant deterioration detection device. Hence, as compared with the case in which lubricant deterioration detection devices are separately installed for a plurality of bearing housings, the install space can be reduced, and periodic filter exchange can be performed for a single filter 201 to simplify the maintenance.

As apparent from the graph in FIG. 28C, the aldehyde concentration determined by the gas sensor 1 is substantially 0 for a while after the rotation start of the bearing and exceeds 1.0 ppm only after 195 hours. Hence, by setting the lubricant deterioration detection device illustrated in FIG. 31 to switch the flow path switching pipe 47 in such a way as to enable connection to each gas inlet portion 410 once or more between 195 hours and 206 hours, the lubricant deterioration can be correctly determined. The same threshold can be used for a plurality of bearings used in different conditions, and thus complicated threshold setting can be simplified. An example threshold is 1.0 ppm as described above.

Fourth Aspect

Fourth Embodiment

An embodiment in a fourth aspect of the present invention will now be described, but the invention is not limited to the following embodiment. The following embodiment includes technically preferred limitations for carrying out the invention, but the limitations are not essential requirements of the invention.

Figure 32:
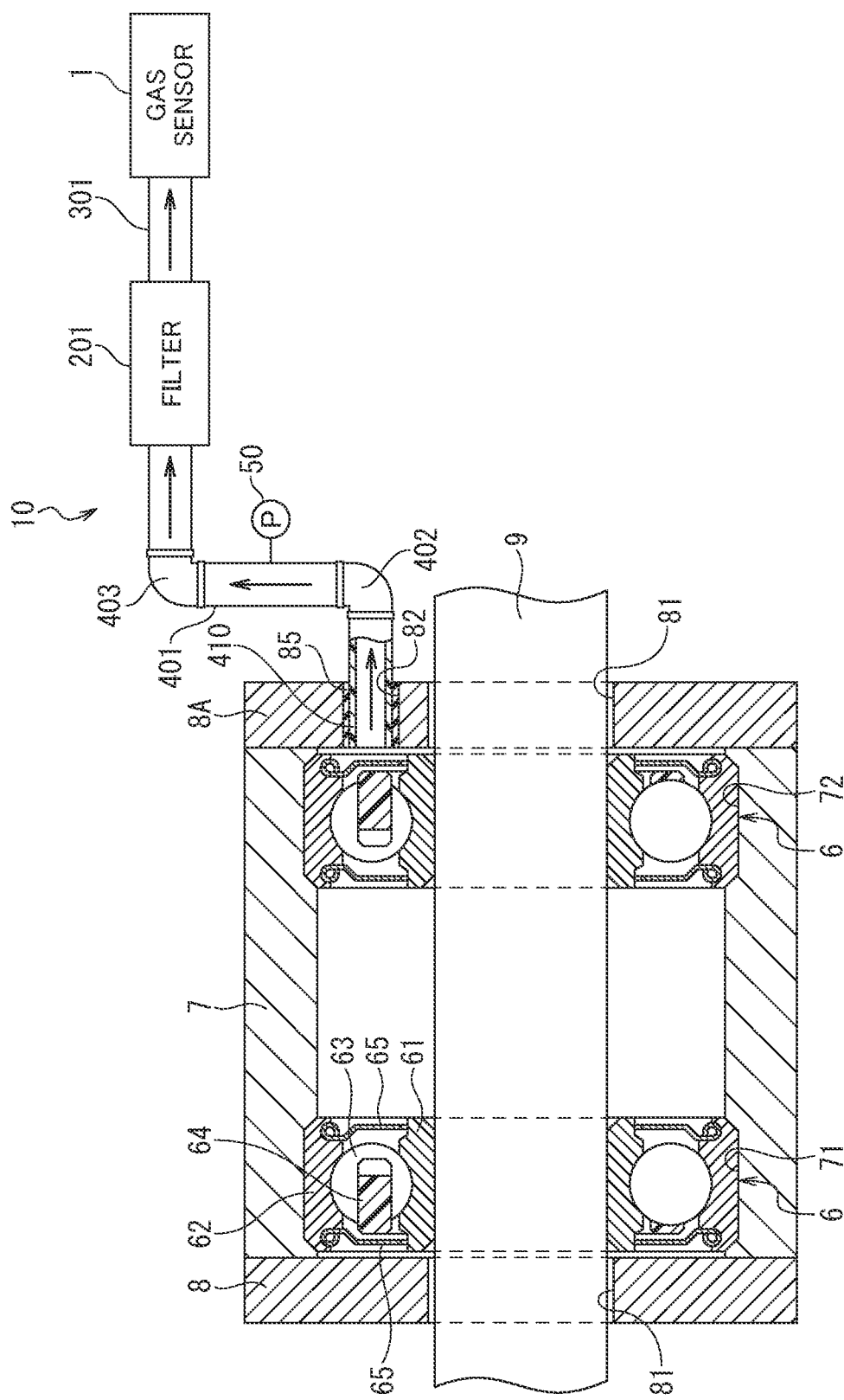
FIG. 32 is a view illustrative of a lubricant deterioration detection device of a fourth embodiment in use where a gas outlet port is formed on a circular plate portion of a housing.
Figure 33:
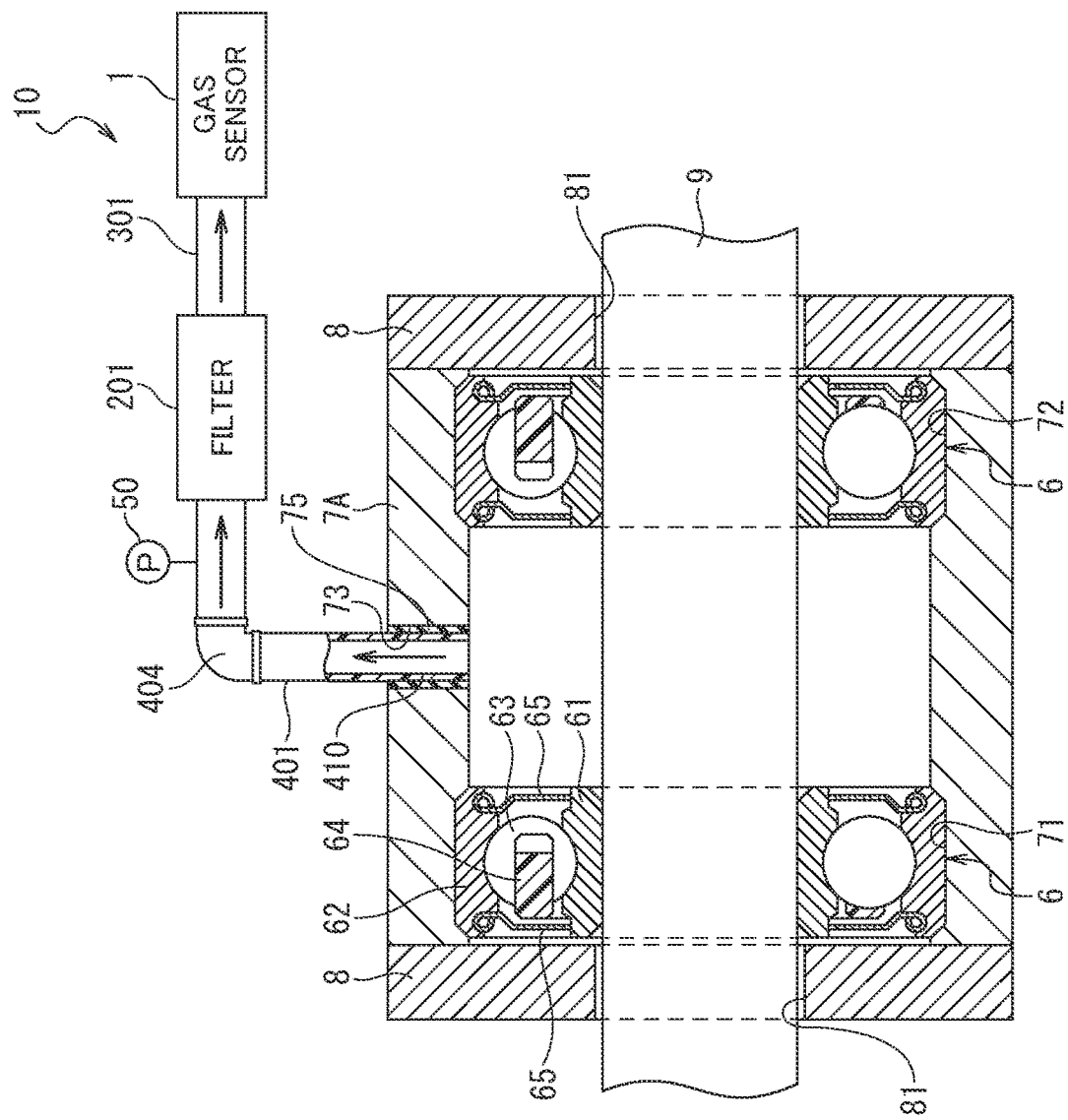
FIG. 33 is a view illustrative of a lubricant deterioration detection device of a fourth embodiment in use where a gas outlet port is formed on a cylinder portion of a housing.

As illustrated in FIG. 32 and FIG. 33, the lubricant deterioration detection device 10 of the embodiment includes a gas sensor 1, a filter 201, gas inlet pipes 301, 401, and a suction pump 50. The gas inlet pipe 301 connects a gas inlet port of the gas sensor 1 and a gas outlet port of the filter 201. One end of the gas inlet pipe 401 is a gas inlet portion 410 that is a connector to the housing described later, and the other end is connected to a gas inlet port of the filter 201.

In the example in FIG. 32, the gas inlet pipe 401 includes three straight pipes and two elbow pipes, extends through an elbow pipe 402 in the direction perpendicular to the extending direction of the gas inlet portion 410, and extends through an elbow pipe 403 in the same direction as the extending direction of the gas inlet portion 410. The suction pump 50 is connected to a point between the elbow pipes 402, 403 of the gas inlet pipe 401. In the example in FIG. 33, the gas inlet pipe 401 includes two straight pipes and an elbow pipe and extends through an elbow pipe 404 to a direction perpendicular to the extending direction of the gas inlet portion 410. The suction pump 50 is connected to a point between the elbow pipe 404 of the gas inlet pipe 401 and the filter 201.

The gas sensor 1 is a controlled potential electrolysis sensor that detects only aldehydes (carbonyl compounds). The gas sensor 1 includes a display device that displays a real time aldehyde concentration. As the filter 201, a ceramic filter that removes oil mist (oil removal portion) is provided.

The lubricant deterioration detection device 10 includes a housing that rotatably stores two rolling bearings 6. The housing in the example in FIG. 32 includes a cylinder portion 7 and circular plate portions 8, 8A each having a central hole 81, and the housing in the example in FIG. 33 includes a cylinder portion 7A and two identical circular plate portions 8 each having a central hole 81.

Each of the two rolling bearings 6 is a sealed deep groove ball bearing including an inner ring 61, an outer ring 62, balls (rolling elements) 63, a retainer 64, and shield plates (noncontact seals) 65 and is lubricated with a lubricant. At the respective axial ends of the cylinder portion 7 on the inner peripheral surface, grooves 71, 72 are formed for fitting the outer rings 62 of the two rolling bearings 6.

The circular plate portion 8A included in the housing in the example in FIG. 32 has a through hole 82 penetrating in the axis direction at a position facing a shield plate 65. The cylinder portion 7A included in the housing in the example in FIG. 33 has a through hole 73 penetrating in a direction orthogonal to the axis, at the axial center.

The two rolling bearings 6 are fixed to the cylinder portion 7 apart from each other in the axis direction by fitting the outer rings 62 to the corresponding grooves 71, 72. The respective axial ends of the cylinder portion 7 are closed by the circular plate portions 8, 8A in the example in FIG. 32 or by the two circular plate portions 8 in the example in FIG. 33. A rotating shaft 9 fitted to the inner rings 61 of the two rolling bearings 6 penetrates the central holes 81, extends outward from the circular plate portions 8, 8A in the example in FIG. 32 or extends outward from the two circular plate portions 8 in the example in FIG. 33, and is connected to a rotation device not shown in the drawings.

In the example in FIG. 32, the gas inlet portion 410 of the gas inlet pipe 401 is inserted through a cylindrical-shaped rubber member 85 into the through hole 82 of the circular plate portion 8A, and the gap between the gas inlet portion 410 and the through hole 82 is sealed by the rubber member 85. In the example in FIG. 33, the gas inlet portion 410 of the gas inlet pipe 401 is inserted through a cylindrical-shaped rubber member 75 into the through hole 73 of the cylinder portion 7A, and the gap between the gas inlet portion 410 and the through hole 73 is sealed by the rubber member 75.

The lubricant deterioration detection device 10 functions as follows: By activating the suction pump 50 concurrently with the rotation start of the rolling bearings 6, the gas in the housing is sucked. The sucked gas passes through the gas inlet pipe 401 into the filter 201, and the filter 201 removes oil mist. Subsequently, the gas passes through the gas inlet pipe 301 into the gas sensor 1, then the gas sensor 1 determines the aldehyde concentration, and the result is displayed.

The aldehyde concentration of a gas sucked into the gas inlet pipe 401 of the lubricant deterioration detection device 10 is substantially 0 before deterioration of a lubricant in the rolling bearings 6, gradually increases just before seizing up by the lubricant, and then increases sharply. Hence, the deterioration of a lubricant in the rolling bearings 6 can be identified when the gas sensor 1 starts to detect increasing aldehyde concentrations.

In the lubricant deterioration detection device 10 of the embodiment, the gas sensor 1 is provided outside the housing rotatably storing the rolling bearings 6, thus is unlikely to be affected by vibration or heat generated during operation of the rolling bearings 6, and is unlikely to cause malfunction or failure. Accordingly, the lubricant deterioration detection device can determine the deterioration state of a lubricant in a rolling bearing with higher accuracy than a lubricant deterioration detection device in which the housing of a gas sensor is directly attached to a rolling bearing.

If a lubricant or components other than the components generated from a lubricant adhere to the gas sensor 1, the gas sensor 1 may malfunction, or the detection accuracy of the gas sensor 1 may deteriorate. To address this, in the lubricant deterioration detection device 10 of the embodiment, the gas inlet port of the gas sensor 1 is not directly connected to the through hole 82, 73 as the gas outlet port of the housing through a gas inlet pipe, but the filter 201 is provided therebetween. The gas inlet port of the gas sensor 1 is connected to the gas outlet port of the filter 201 through the gas inlet pipe 301, and the through hole 82, 73 of the housing is connected to the gas inlet port of the filter 201 through the gas inlet pipe 401. As the filter 201, an oil mist-removing filter is provided.

The gas sensor 1 is thus unlikely to be affected by oil mist generated during operation of the rolling bearing 6 and is unlikely to cause malfunction or failure. Accordingly, the lubricant deterioration detection device 10 of the embodiment can determine the deterioration state of a lubricant in a rolling bearing with higher accuracy than a lubricant deterioration detection device in which the gas inlet port of a gas sensor is directly connected to the gas outlet port of a housing through a pipe.

In place of the oil mist-removing filter, a wet dust collector or a static oil mist remover may be provided.

Examples of the oil mist-removing filter include a paper filter, a metal filter, a ceramic filter, and a CNP filter. Of these filters, a paper filter is preferably used in terms of easy exchange. As the paper filter, a paper filter having a mesh size of about 200 and capable of collecting oil mist particles having a particle size of 0.3 μm or more is preferably used.

Between the gas sensor 1 and the gas inlet portion 410, a filter that removes smelling components other than aldehydes (smell removal portion) may be provided. Examples of the filter that removes smelling components other than aldehydes (for example, smelling components generated from industrial wastes of factories) include a photocatalytic filter and an activated carbon filter. Specifically preferred is a filter in which an adsorbent and a photocatalytic powder are packed in the space (cavities) between a nonwoven fabric and a film. The adsorbent is preferably activated carbon and silica gel, and the photocatalyst is preferably titanium oxide and zinc oxide.

Alternatively, the difference between a gas having passed through a filter that adsorbs aldehydes, such as a dinitrophenylhydrazine (DNPH) filter, and a gas not having passed can be analyzed to determine aldehydes.

<Verification Test of Lubricant Deterioration Detection by Lubricant Deterioration Detection Device 10>

The device illustrated in FIG. 34 was used to perform the verification test for examining the lubricant deterioration detection result by the lubricant deterioration detection device 10. The device illustrated in FIG. 34 is prepared as follows: the elbow pipe 402 that connects a portion of the gas inlet pipe 401 with the suction pump 50 to the gas inlet portion 410 in the example in FIG. 32 is replaced with a branch pipe 405, and the opposite side of the branch pipe 405 to the gas inlet pipe 401 is connected to one end of a gas inlet pipe 104 included in a lubricant deterioration detection device 100 of a comparative example. As the electrode included in the controlled potential electrolysis sensor of the gas sensor 1, a platinum electrode was used.

The lubricant deterioration detection device 100 includes a smell sensor 101, a filter 102, gas inlet pipes 103, 104, and a suction pump 105. The gas inlet pipe 103 connects a gas inlet port of the smell sensor 101 and a gas outlet port of the filter 102. The other end of the gas inlet pipe 104 is connected to a gas inlet port of the filter 102. The suction pump 105 is connected to a portion of the gas inlet pipe 104 connected to the branch pipe 405. The smell sensor 101 is an indium oxide-based heat ray sintered semiconductor sensor and can determine odor index. As the filter 102, the same oil mist-removing filter as the filter 201 was used.

As two rolling bearings 6, rolling bearings each having an inner diameter of 25 mm, an outer diameter of 62 mm, and a width of 17 mm were prepared. Each rolling bearing 6 was lubricated with a grease. The grease used was a commercially available grease containing a lithium soap (consistency: No. 2) as a thickener and a mineral oil (dynamic viscosity at 40° C.: 100 mm$^2$/s) as a base oil.

The outer ring 62 of each rolling bearing 6 was fitted to the corresponding groove 71, 72 on the cylinder portion 7, a rotating shaft 9 of a tester is fitted to the inside of the inner ring 61 of each rolling bearing 6, and the gas inlet portion 410 of the lubricant deterioration detection devices 10, 100 was attached to the circular plate portion 8A, giving the state illustrated in FIG. 34. The through hole 82 in the circular plate portion 8A has a diameter of 6.5 mm, and the gas inlet pipe 401 has an outer diameter of 6 mm and an inner diameter of 4 mm. The gap between the through hole 82 and the gas inlet pipe 401 is sealed by a rubber member 85.

While a radial load of 98 N and an axial load of 1,470 N were applied to each rolling bearing 6, the rotating shaft 9 was continuously rotated at a rotation speed of 10,000 $min^{-1}$. Concurrently with the rotation start of the rotating shaft 9, the lubricant deterioration detection devices 10, 100 were driven, and the aldehyde concentration detection by the gas sensor 1, the odor index measurement by the smell sensor 101, and the outer ring temperature measurement were continuously performed. The results are illustrated as the graphs in FIGS. 35A to 35C. The rotation of the rotating shaft 9 and the driving of the lubricant deterioration detection devices 10, 100 were so controlled as to be stopped when an abnormal increase of the outer ring temperature was detected.

At 208 hours after the test start, an abnormal increase of the outer ring temperature was detected, and the rotation of the rotating shaft 9 and the driving of the lubricant deterioration detection devices 10, 100 were stopped.

Figure 35A:
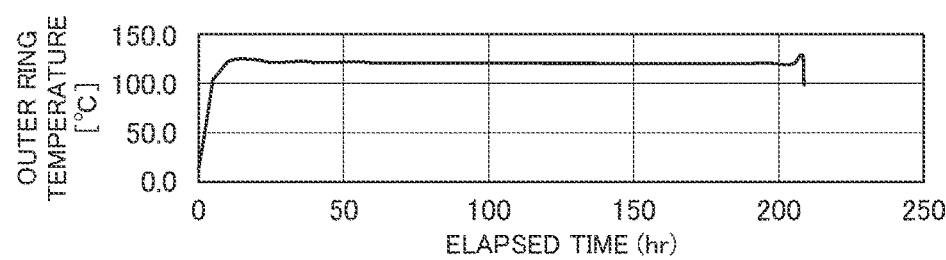
FIGS. 35A to 35C are graphs obtained by a test performed in the fourth embodiment.
Figure 35B:
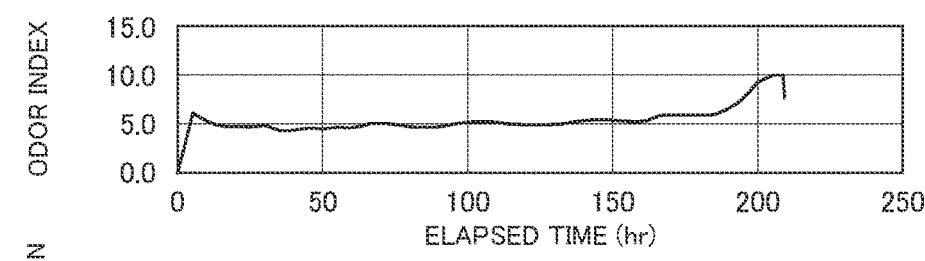
Figure 35C:
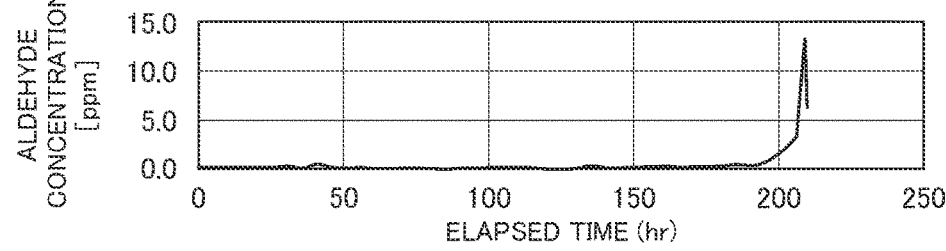

The graphs in FIGS. 35A to 35C reveal the following findings.

FIG. 35A is a graph illustrating the relation between elapsed time and outer ring temperature. The outer ring temperature increased after the test start, then was almost constant from about 10 hours, and exceeded 125° C. at 208 hours.

FIG. 35B is a graph illustrating the relation between elapsed time and odor index detected by the smell sensor 101. The odor index increased at substantially the same rate as the increase rate of the outer ring temperature and then was almost constant at around 5.0 when the outer ring temperature became almost constant. Subsequently, the odor index slightly increased at around 165 hours, then was constant at about 6.0, and started to increase from 185 hours.

FIG. 35C is a graph illustrating the relation between elapsed time and aldehyde concentration determined by the gas sensor 1. The aldehyde concentration was almost 0 immediately after the test start until 180 hours, then gradually increased from 180 hours, and sharply increased from 206 hours that was immediately before the detection of the abnormal increase of the outer ring temperature.

The test results reveal the following findings.

The lubricant deterioration detection devices 10, 100 can identify lubricant deterioration in advance.

With the lubricant deterioration detection device 10 of the embodiment, the aldehyde concentration was substantially 0 immediately after the test start until lubricant deterioration was caused in the rolling bearings 6, gradually increased just before seizing up by the lubricant, and then increased sharply. Hence, the deterioration of a lubricant in the rolling bearings 6 can be identified when the gas sensor 1 starts to detect increasing aldehyde concentrations.

With the lubricant deterioration detection device 100 of the comparative example, the odor index increased immediately after the test start, then was almost constant before lubricant deterioration was caused in the rolling bearings 6, and gradually increased just before seizing up by the lubricant. Hence, by setting the threshold of the odor index at, for example, 7.0, lubricant deterioration in the rolling bearings 6 can be identified when the odor index reaches the threshold. In other words, the lubricant deterioration detection device 100 of the comparative example can previously detect lubricant deterioration. In other words, the lubricant deterioration detection device 100 of the comparative example needs previous threshold setting depending on conditions of use. In addition, the odor index varies with conditions of use of a rolling bearing, and thus an apparatus including a plurality of rolling bearings needs threshold setting for the respective bearings, which is a complicated process.

As described above, the lubricant deterioration detection device 100 of the comparative example needs previous threshold setting, and thus a setting error of the threshold may lead to incorrect determination of lubricant deterioration. In contrast, the lubricant deterioration detection device 10 of the embodiment eliminates the necessity of threshold setting depending on conditions of use. An example of the threshold is 1.0 ppm from the graph in FIG. 35C. Hence, the lubricant deterioration detection device 10 of the embodiment can determine the deterioration state of a lubricant with higher accuracy than the lubricant deterioration detection device 100 of the comparative example.

Alternative Embodiment

Figure 36:
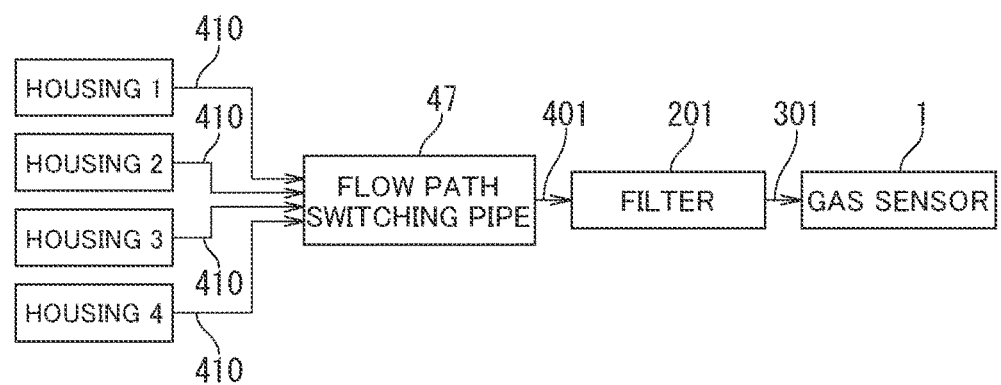
FIG. 36 is a view illustrating a single lubricant deterioration detection device capable of evaluating lubricant deterioration of rolling bearings in a plurality of housings.

A lubricant deterioration detection device of an alternative embodiment illustrated in FIG. 36 is prepared as follows: the elbow pipe 402 that connects a portion of the gas inlet pipe 401 with the suction pump 50 to the gas inlet portion 410 in the lubricant deterioration detection device 10 in FIG. 32 is replaced with a flow path switching pipe 47, and the flow path switching pipe 47 is connected to a plurality of gas inlet portions 410. Each of the plurality of gas inlet portions 410 is inserted into a through hole 73 (82) formed in a corresponding housing (a cylinder portion 7 or a circular plate portion 8A) through a rubber member 75 (85), and the gap between the gas inlet portion 410 and the through hole 73 (82) is sealed.

In the example illustrated in FIG. 36, by switching the flow path switching pipe 47, the aldehyde concentrations contained in gases in the plurality of housings can be determined by a single gas sensor 1. In other words, lubricant deterioration of rolling bearings rotatably stored in a plurality of housings can be evaluated by a single lubricant deterioration detection device. Hence, as compared with the case in which lubricant deterioration detection devices are separately installed for a plurality of housings, the install space can be reduced, and periodic filter exchange can be performed for a single filter 201 to simplify the maintenance.

As apparent from the graph in FIG. 35C, the aldehyde concentration determined by the gas sensor 1 is substantially 0 for a while after the rotation start of the bearing and exceeds 1.0 ppm only after 195 hours. Hence, by setting the lubricant deterioration detection device illustrated in FIG. 36 to switch the flow path switching pipe 47 in such a way as to enable connection to each gas inlet portion 410 once or more between 195 hours and 206 hours, the lubricant deterioration can be correctly determined. The same threshold can be used for a plurality of bearings used in different conditions, and thus complicated threshold setting can be simplified. An example threshold is 1.0 ppm as described above.

REFERENCE SIGNS LIST

1 Gas sensor
11 First channel
12 Second channel
13 Third channel
14 Fourth channel 2 Radio transmitter
20 Display device (receiver)
21 Circuit board
211 Signal processing circuit
212 Transmission circuit
213 Antenna
214 Charging circuit
215 Secondary battery
22 Power line
23 Power line
24 Signal processing line
3 Thermoelectric conversion element
32 Substrate of thermoelectric conversion element
310 Thermoelectric conversion unit of thermoelectric conversion element
4 (4A, 4B) Rolling bearing
41 Inner ring
42 Outer ring
43 Ball
44 Retainer
45 Shield plate
5 Cylinder (bearing housing)
51, 52 Groove
60 Wiring
70 Wiring
201 Filter
301 Gas inlet pipe
401 Gas inlet pipe
410 Gas inlet portion
50 Suction pump
6 Rolling bearing
61 Inner ring
62 Outer ring
63 Ball
64 Retainer
65 Shield plate
7 Cylinder portion of housing (bearing housing)
71, 72 Groove
73 Through hole (gas outlet port)
75 Rubber member
8 Circular plate portion of housing (bearing housing)
8A Circular plate portion of housing (bearing housing)
82 Through hole (gas outlet port)
85 Rubber member
9 Rotating shaft
10 Lubricant deterioration detection device
100 Lubricant deterioration detection device

The invention claimed is:

1. A lubricant deterioration detection device comprising a gas sensor configured to detect a carbonyl compound, wherein the gas sensor is configured to detect the carbonyl compound selected from at least one of formaldehyde, acetaldehyde, propanal, butanal, pentanal, n-hexanal, n-heptanal, formic acid, and acetic acid, and
wherein the detection deterioration device further comprises an oil removal portion that removes an oil mist generated from the lubricant during operation of the rolling bearing in the rolling bearing due to lubricant deterioration.

2. The lubricant deterioration detection device according to claim 1, wherein the gas sensor includes a plurality of channels containing a channel that selectively detects the carbonyl compound.

3. The lubricant deterioration detection device according to claim 1, comprising:
a housing rotatably storing a rolling bearing; and
a gas inlet pipe connecting a gas outlet port formed on the housing to a gas inlet port of the gas sensor and configured to introduce a gas in the housing into the gas sensor, wherein
the gas sensor is located outside the housing, and a deterioration state of a lubricant in the rolling bearing is detected by a detected value of the gas sensor.

4. The lubricant deterioration detection device according to claim 3, wherein the gas inlet pipe is connected to the gas sensor through an oil removal portion that removes an oil contained in the introduced gas.

5. The lubricant deterioration detection device according to claim 3, wherein a gas outlet port of the housing is connected to the gas inlet port of the gas sensor through a flow path switching pipe.

6. The lubricant deterioration detection device according to claim 1, further comprising
a radio transmitter that wirelessly transmits a detection result by the gas sensor to a receiver, and
a stand-alone power supply that includes a thermoelectric conversion element and supplies electric power to the gas sensor and the radio transmitter.

7. A lubricant deterioration state evaluation method comprising:
detecting a carbonyl compound selected from at least one of formaldehyde, acetaldehyde, propanal, butanal, pentanal, n-hexanal, n-heptanal, formic acid, and acetic acid by a gas sensor,
wherein a gas is introduced into a gas sensor after an oil mist generated from the lubricant during operation of the rolling bearing in the rolling bearing due to lubricant deterioration is removed from the gas by an oil removal portion.

* * * * *